United States Patent
Seo et al.

(10) Patent No.: US 10,704,027 B2
(45) Date of Patent: Jul. 7, 2020

(54) BACTERIOPHAGE AND ANTIBACTERIAL COMPOSITION COMPRISING THE SAME

(71) Applicant: CJ CHEILJEDANG CORPORATION, Seoul (KR)

(72) Inventors: Hyo Seel Seo, Wonju-si (KR); Eun Mi Shin, Seoul (KR); Gi Duk Bae, Seoul (KR); Jae Won Kim, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/925,633

(22) Filed: Mar. 19, 2018

(65) Prior Publication Data

US 2018/0282703 A1 Oct. 4, 2018

Related U.S. Application Data

(63) Continuation of application No. 14/770,328, filed as application No. PCT/KR2014/001535 on Feb. 25, 2014, now Pat. No. 9,938,506.

(30) Foreign Application Priority Data

Feb. 27, 2013 (KR) .......................... 10-2013-0021501

(51) Int. Cl.

| C12N 7/00 | (2006.01) |
| A61K 35/76 | (2015.01) |
| A23K 50/75 | (2016.01) |
| A01N 63/00 | (2020.01) |
| C11D 3/48 | (2006.01) |

(52) U.S. Cl.
CPC ............... *C12N 7/00* (2013.01); *A01N 63/00* (2013.01); *A23K 50/75* (2016.05); *A61K 35/76* (2013.01); *C11D 3/48* (2013.01); *C12N 2795/00021* (2013.01); *C12N 2795/00031* (2013.01); *C12N 2795/00032* (2013.01); *C12N 2795/10221* (2013.01); *C12N 2795/10222* (2013.01); *C12N 2795/10231* (2013.01); *Y02A 50/473* (2018.01)

(58) Field of Classification Search
None
See application file for complete search history.

(56) References Cited

U.S. PATENT DOCUMENTS

| 6,322,783 | B1 | 11/2001 | Takahashi | |
| 6,485,902 | B2 | 11/2002 | Waddell et al. | |
| 8,597,928 | B2 | 12/2013 | Yang et al. | |
| 9,358,258 | B2 | 6/2016 | Kim et al. | |
| 9,657,277 | B2 * | 5/2017 | Shin ..................... | A23L 2/44 |
| 9,745,555 | B2 | 8/2017 | Son et al. | |
| 9,758,767 | B2 | 9/2017 | Son et al. | |
| 9,862,935 | B2 * | 1/2018 | Shin ..................... | C12N 7/00 |
| 9,938,506 | B2 * | 4/2018 | Seo ..................... | A23K 50/75 |
| 9,950,018 | B2 * | 4/2018 | Shin ..................... | A23K 20/195 |
| 9,956,256 | B2 * | 5/2018 | Shin ..................... | A23K 10/18 |
| 9,968,506 | B2 * | 5/2018 | Cruz ..................... | A61H 1/0288 |
| 10,166,264 | B2 * | 1/2019 | Yang ..................... | A61K 35/76 |
| 10,240,129 | B2 * | 3/2019 | Shin ..................... | A23K 10/18 |
| 10,265,353 | B2 * | 4/2019 | Yoon ..................... | A61K 35/76 |
| 10,286,020 | B2 * | 5/2019 | Shin ..................... | A23K 20/195 |
| 2011/0052542 | A1 | 3/2011 | Shin et al. | |
| 2014/0348799 | A1 | 11/2014 | Yang et al. | |
| 2014/0356330 | A1 | 12/2014 | Kim et al. | |
| 2014/0377842 | A1 | 12/2014 | Kim et al. | |
| 2016/0076003 | A1 | 3/2016 | Son et al. | |
| 2016/0076004 | A1 | 3/2016 | Son et al. | |
| 2016/0083695 | A1 | 3/2016 | Seo et al. | |
| 2017/0035817 | A1 | 2/2017 | Shin et al. | |
| 2017/0037382 | A1 | 2/2017 | Shin et al. | |
| 2017/0128504 | A1 * | 5/2017 | Yang ..................... | A61K 35/76 |
| 2017/0189459 | A1 | 7/2017 | Shin et al. | |
| 2017/0189460 | A1 | 7/2017 | Shin et al. | |
| 2017/0333498 | A1 | 11/2017 | Yoon et al. | |
| 2018/0282703 | A1 * | 10/2018 | Seo ..................... | A23K 50/75 |
| 2019/0153399 | A1 * | 5/2019 | Shin ..................... | A23K 10/18 |
| 2019/0224258 | A1 * | 7/2019 | Shin ..................... | A23K 10/18 |

FOREIGN PATENT DOCUMENTS

| KR | 10-2009-0021475 A | 3/2009 |
| KR | 10-2009-0030532 A | 3/2009 |
| KR | 10-2009-0035861 A | 4/2009 |
| KR | 10-0910961 B1 | 8/2009 |
| KR | 10-2009-0127655 A | 12/2009 |
| KR | 10-1023995 B1 | 3/2011 |
| KR | 10-2012-0013149 A | 2/2012 |

(Continued)

OTHER PUBLICATIONS

Tsonos et al, Veterinary Microbiology 171 (2014) 470-479. (Year: 2014).*
Notice of Allowance dated Mar. 27, 2014 of corresponding Korean Patent Application No. 10-2013-0021501—1 page.
Dho-Moulin et al, "Avian pathogenic *Escherichia coli* (APEC)", Veterinary Research, BioMed Central, 1999, vol. 30 (2-3), pp. 299-316.

(Continued)

*Primary Examiner* — Nita M. Minnifield

(74) *Attorney, Agent, or Firm* — Knobbe Martens Olson & Bear LLP

(57) ABSTRACT

Provided is a novel bacteriophage ΦCJ23 (KCCM11365P). In addition, the present invention relates to an antibacterial composition including the bacteriophage ΦCJ23 (KCCM11365P) as an active ingredient. Further, provided is a method of preventing and/or treating infectious diseases by avian pathogenic *Escherichia coli*(APEC) in birds using the bacteriophage ΦCJ23(KCCM11365P) or the antibacterial composition containing the bacteriophage ΦCJ23 (KCCM11365P) as an active ingredient.

7 Claims, 6 Drawing Sheets

Specification includes a Sequence Listing.

(56) References Cited

FOREIGN PATENT DOCUMENTS

| KR | 10-2012-0111535 A | 10/2012 | |
|---|---|---|---|
| WO | 88/09669 A1 | 12/1988 | |
| WO | WO-2013157813 A1 * | 10/2013 | ............. A61K 35/76 |
| WO | WO-2014133301 A1 * | 9/2014 | ............. A23K 50/75 |

OTHER PUBLICATIONS

Dziva et al., "Colibacillosis in poultry: unravelling the molecular basis of virulence of avian pathogenic *Escherichia coil* in their natural hosts", Avian Pathology, Aug. 2008, vol. 37, Issue 4, pp. 355-366.
Lau et al., "Efficacy of a bacteriophage isolated from chickens as a therapeutic agent for colibacillosis in broiler chickens", Poultry Science, 2010, vol. 89, pp. 2589-2596.
Cislo et al., "Archivum Immunologiae et Therapiae Experimentalis", Ther. Exp., 1987, vol. 2, pp. 175-183 (English Abstract).
Sung Hoon Kim et al., "Bacteriophage, New Alternative Antibiotics", BioWave; Biological Research Information Center, BRIC, 2005, vol. 7, No. 15—10 pages.
Huff et al., "Alternatives to Antibiotics: Ultization of Bacteriophage to treat Colibacillosis and Prevent Foodborne Pathogens", Poultry Science, 2005, vol. 84, pp. 655-659.
Oliveira et al., "Isolation and characterization of bacteriophages for avian pathogenic *E. coli* Strains", Journal of Applied Micriobiology, 2009, vol. 106, pp. 1919-1927.
Jamalludeen et al., "Isolation and characterization of virulent bacteriophages against *Escherichia coli* serogroups O1, O2, and O78", Poultry Science, 2009, vol. 88, pp. 1694-1702.
Li et al., "Complete Genome Sequence of the Novel Lytic Avian Pathogenic Coliphage NJ01", Journal of Virology, Dec. 2012, vol. 86, No. 24, pp. 13874-13875.
Extended European Search Report dated Jun. 24, 2016 of European Patent Application No. 14757633.4—7 pages.
International Search Report dated Apr. 28, 2014 of PCT/KR2014/001535 which is the parent application 4 pages.

* cited by examiner

Figure 6a

| Query | | | | Subject | Score | Identities | Pct |
|---|---|---|---|---|---|---|---|
| Name | Length | Start | End | Description | E-Value | Match/Total | (%) |
| contig00001_orf00004 | 183 | 1 | 165 | hypothetical protein gp2.4 [Escherichia phage vB_EcoP_G7C] | 2E-23 | 51/55 | 92 |
| contig00001_orf00002 | 438 | 1 | 435 | RNA polymerase RNAP1 subunit A [Escherichia phage vB_EcoP_G7C] | 3E-74 | 142/146 | 97 |
| contig00001_orf00001 | 324 | 1 | 321 | hypothetical protein gp1 [Escherichia phage vB_EcoP_G7C] | 8E-46 | 94/107 | 87 |
| contig00001_orf00005 | 129 | 1 | 126 | hypothetical protein gp6 [Escherichia phage vB_EcoP_G7C] | 1E-12 | 37/42 | 88 |
| contig00001_orf00017 | 1218 | 1 | 1215 | RNA polymerase RNAP2 subunit A [Escherichia phage vB_EcoP_G7C] | 0 | 358/406 | 88 |
| contig00001_orf00011 | 315 | 1 | 312 | hypothetical protein gp11 [Escherichia phage vB_EcoP_G7C] | 5E-45 | 84/104 | 80 |
| contig00001_orf00008 | 222 | 1 | 219 | putative phage protein [Escherichia phage vB_EcoP_G7C] | 4E-32 | 64/73 | 87 |
| contig00001_orf00006 | 309 | 1 | 303 | hypothetical protein gp9 [Escherichia phage vB_EcoP_G7C] | 2E-45 | 93/101 | 92 |
| contig00001_orf00015 | 819 | 1 | 816 | RNA polymerase RNAP1 subunit B [Escherichia phage vB_EcoP_G7C] | 9E-152 | 261/272 | 95 |
| contig00001_orf00009 | 258 | 1 | 252 | hypothetical protein gp9.2 [Escherichia phage vB_EcoP_G7C] | 3E-25 | 59/84 | 70 |
| contig00001_orf00013 | 351 | 1 | 348 | hypothetical protein gp14 [Escherichia phage vB_EcoP_G7C] | 1E-60 | 107/116 | 92 |
| contig00001_orf00019 | 879 | 46 | 876 | capsid decorating protein [Escherichia phage vB_EcoP_G7C] | 4E-119 | 220/277 | 79 |
| contig00001_orf00012 | 381 | 1 | 378 | hypothetical protein gp12 [Escherichia phage vB_EcoP_G7C] | 1E-61 | 112/126 | 88 |
| contig00001_orf00018 | 183 | 76 | 180 | hypothetical protein gp16.1 [Escherichia phage vB_EcoP_G7C] | 5E-08 | 25/35 | 71 |
| contig00001_orf00020 | 189 | 1 | 186 | hypothetical protein gp17.1 [Escherichia phage vB_EcoP_G7C] | 4E-28 | 61/62 | 98 |
| contig00001_orf00023 | 186 | 1 | 183 | hypothetical protein gp17.2 [Escherichia phage vB_EcoP_G7C] | 1E-24 | 58/61 | 95 |
| contig00001_orf00027 | 507 | 1 | 504 | dCTP deaminase [Escherichia phage vB_EcoP_G7C] | 6E-87 | 157/168 | 93 |
| contig00001_orf00025 | 1053 | 1 | 1050 | hypothetical protein gp24 [Escherichia phage vB_EcoP_G7C] | 0 | 331/350 | 94 |
| contig00001_orf00026 | 1176 | 1 | 1173 | hypothetical protein gp25 [Escherichia phage vB_EcoP_G7C] | 0 | 374/391 | 95 |
| contig00001_orf00029 | 279 | 91 | 219 | putative membrane immunity protein [Escherichia phage vB_EcoP_G7C] | 6E-17 | 41/43 | 95 |

Figure 6b

| Query | | | | Subject | Score | Identities | Pct |
|---|---|---|---|---|---|---|---|
| Name | Length | Start | End | Description | E-Value | Match/Total | (%) |
| contig00001_orf00031 | 444 | 1 | 441 | hypothetical protein gp29 [Escherichia phage vB_EcoP_G7C] | 6E-70 | 133/147 | 90 |
| contig00001_orf00032 | 945 | 1 | 942 | thymidilate synthase [Escherichia phage vB_EcoP_G7C] | 3E-148 | 261/314 | 83 |
| contig00001_orf00034 | 213 | 1 | 210 | hypothetical protein gp31 [Escherichia phage vB_EcoP_G7C] | 2E-33 | 67/70 | 95 |
| contig00001_orf00037 | 2568 | 1 | 2562 | rIIA-like protein [Escherichia phage vB_EcoP_G7C] | 0 | 734/854 | 85 |
| contig00001_orf00035 | 327 | 1 | 321 | hypothetical protein gp32 [Escherichia phage vB_EcoP_G7C] | 2E-25 | 79/108 | 73 |
| contig00001_orf00045 | 306 | 1 | 297 | hypothetical protein gp40 [Escherichia phage vB_EcoP_G7C] | 1E-46 | 93/99 | 93 |
| contig00001_orf00043 | 531 | 1 | 528 | hypothetical protein gp38 [Escherichia phage vB_EcoP_G7C] | 4E-92 | 168/176 | 95 |
| contig00001_orf00041 | 351 | 1 | 348 | hypothetical protein gp36 [Escherichia phage vB_EcoP_G7C] | 8E-56 | 108/116 | 93 |
| contig00001_orf00048 | 981 | 1 | 978 | hypothetical protein gp42 [Escherichia phage vB_EcoP_G7C] | 1E-178 | 316/326 | 96 |
| contig00001_orf00044 | 2580 | 1 | 2577 | DNA polymerase [Escherichia phage vB_EcoP_G7C] | 0 | 830/859 | 96 |
| contig00001_orf00051 | 804 | 1 | 687 | ssDNA-binding protein [Escherichia phage vB_EcoP_G7C] | 1E-110 | 215/229 | 93 |
| contig00001_orf00050 | 753 | 1 | 750 | hypothetical protein gp44 [Escherichia phage vB_EcoP_G7C] | 8E-138 | 246/250 | 98 |
| contig00001_orf00042 | 1311 | 1 | 1308 | DNA helicase [Escherichia phage vB_EcoP_G7C] | 0 | 423/436 | 97 |
| contig00001_orf00040 | 396 | 1 | 393 | hypothetical protein gp35 [Escherichia phage vB_EcoP_G7C] | 1E-61 | 119/131 | 90 |
| contig00001_orf00039 | 2049 | 1 | 2046 | rIIB-like protein [Escherichia phage vB_EcoP_G7C] | 0 | 576/663 | 84 |
| contig00001_orf00055 | 123 | 1 | 120 | hypothetical protein gp47.2 [Escherichia phage vB_EcoP_G7C] | 5E-13 | 34/40 | 85 |
| contig00001_orf00053 | 441 | 1 | 294 | hypothetical protein gp47 [Escherichia phage vB_EcoP_G7C] | 2E-25 | 73/103 | 70 |
| contig00001_orf00049 | 2154 | 1 | 2151 | DNS protein [Escherichia phage vB_EcoP_G7C] | 0 | 695/717 | 96 |
| contig00001_orf00047 | 498 | 1 | 495 | putative HNH homing endonuclease [Escherichia phage vB_EcoP_G7C] | 1E-90 | 160/165 | 96 |
| contig00001_orf00052 | 555 | 1 | 552 | hypothetical protein gp46 [Escherichia phage vB_EcoP_G7C] | 1E-98 | 181/184 | 98 |
| contig00001_orf00063 | 444 | 1 | 441 | putative structural protein [Escherichia phage vB_EcoP_G7C] | 1E-47 | 109/153 | 71 |
| contig00001_orf00065 | 843 | 7 | 840 | putative tail protein [Escherichia phage vB_EcoP_G7C] | 5E-136 | 265/278 | 95 |
| contig00001_orf00061 | 10713 | 2713 | 10710 | virion RNA polymerase [Escherichia phage vB_EcoP_G7C] | 0 | 2410/2686 | 89 |

Figure 6c

| Query | | | | Subject | Score | Identities | Pct |
|---|---|---|---|---|---|---|---|
| Name | Length | Start | End | Description | E-Value | Match/Total | (%) |
| contig00001_orf00071 | 345 | 1 | 342 | hypothetical protein gp58 [Escherichia phage vB_EcoP_G7C] | 2E-57 | 113/114 | 99 |
| contig00001_orf00070 | 1221 | 1 | 1218 | hypothetical protein gp57 [Escherichia phage vB_EcoP_G7C] | 8E-170 | 386/406 | 95 |
| contig00001_orf00086 | 642 | 1 | 639 | hypothetical protein gp55 [Escherichia phage vB_EcoP_G7C] | 5E-102 | 206/213 | 96 |
| contig00001_orf00064 | 2655 | 1 | 2652 | hypothetical protein gp53 [Escherichia phage vB_EcoP_G7C] | 0 | 810/867 | 91 |
| contig00001_orf00059 | 519 | 37 | 513 | gp49 [Enterobacteria phage N4] | 2E-85 | 144/159 | 90 |
| contig00001_orf00069 | 1203 | 1 | 1200 | major coat protein [Escherichia phage vB_EcoP_G7C] | 0 | 389/400 | 97 |
| contig00001_orf00072 | 2271 | 1 | 2268 | portal protein [Escherichia phage vB_EcoP_G7C] | 0 | 735/761 | 96 |
| contig00002_orf00005 | 348 | 1 | 342 | hypothetical protein gp71 [Escherichia phage vB_EcoP_G7C] | 1E-51 | 99/114 | 86 |
| contig00002_orf00002 | 1590 | 1 | 1587 | terminase subunit A [Escherichia phage vB_EcoP_G7C] | 0 | 521/529 | 98 |
| contig00001_orf00074 | 636 | 1 | 633 | N-acetylmuramidase [Escherichia phage vB_EcoP_G7C] | 4E-103 | 199/211 | 94 |
| contig00001_orf00073 | 225 | 2 | 169 | putative Rz/Rz1 spanin protein [Escherichia phage vB_EcoP_G7C] | 5E-24 | 55/56 | 98 |
| contig00001_orf00075 | 330 | 49 | 321 | hypothetical protein gp63 [Escherichia phage vB_EcoP_G7C] | 2E-21 | 66/91 | 72 |
| contig00002_orf00001 | 711 | 1 | 708 | putative tail protein [Escherichia phage vB_EcoP_G7C] | 4E-134 | 232/236 | 98 |
| contig00002_orf00003 | 690 | 1 | 687 | hypothetical protein gp69 [Escherichia phage vB_EcoP_G7C] | 5E-114 | 223/229 | 97 |
| contig00002_orf00004 | 279 | 1 | 276 | hypothetical protein gp70 [Escherichia phage vB_EcoP_G7C] | 3E-27 | 69/92 | 75 |
| contig00002_orf00006 | 315 | 1 | 312 | hypothetical protein gp71.1 [Escherichia phage vB_EcoP_G7C] | 2E-43 | 84/104 | 80 |
| contig00003_orf00004 | 2115 | 64 | 2112 | tailspike protein [Escherichia phage vB_EcoM_CBA120] | 0 | 510/689 | 74 |

# BACTERIOPHAGE AND ANTIBACTERIAL COMPOSITION COMPRISING THE SAME

TECHNICAL FIELD

The present invention relates to a novel bacteriophage having a specific bacteriocidal activity against avian pathogenic *Escherichia coli* (APEC) and antibacterial composition comprising the same. In addition, the present invention relates to a method of preventing or treating poultry diseases using the novel bacteriophage or the antibacterial composition.

BACKGROUND ART

*Escherichia coli* (hereinafter referred to as '*E. coli*') is a Gram-negative, short rod-shaped bacterium belonging to the genus *Escherichia* and the family Enterobacteriaceae, and is one of the normal flora existing in the intestines of various animals including mammals. It was known that most of the strains of *E. coli* are non-pathogenic and may cause opportunistic infections, but some highly pathogenic strains cause diverse intestinal diseases and septicemia in animals including humans.

It was known that among these *E. coli* strains, particularly, avian pathogenic *E. coli*(APEC), which is *E. coli* infected through respiratory tract of birds, for example, chickens, ducks, turkeys, or the like, infiltrates into the body through respiratory mucosa. APEC causes various diseases such as septicemia, granuloma, airsacculitis, salpingitis, arthritis, or the like, in birds. Particularly, APEC causes significant economic damage to a poultry industry in that APEC causes respiratory diseases mainly in poultry, or the like, such that APEC becomes a problem.

Meanwhile, bacteriophage is a specialized type of virus that infects and destroys only bacteria, and can self-replicate only inside host bacteria. The bacteriophage has strong host specificity as compared to antibiotics, and recently, a problem of emergence of resistant bacteria against use of antibiotics has been serious, such that an interest in practical use of the bacteriophage has increased (Non-Patent Documents 1 and 2).

Therefore, research regarding the bacteriophage has been actively conducted in many countries around the world, and in addition to a patent application for bacteriophage, an attempt to acquire Food and Drug Administration (FDA) approval for a composition containing the bacteriophage has been gradually increased.

As the prior art for the bacteriophage, 7 kinds of bacteriophages for controlling *E. coli* 0157:H have been disclosed in Patent Document 1, and a bacteriophage having a specific bacteriocidal activity against Staphylococcus aureus has been disclosed in Patent Document 2. Further, lytic protein derived from a bacteriophage specifically destroying a peptidoglycan structure of bacterial cell membrane, and bacteria lysates by the lytic protein have been disclosed in Patent Document 3.

However, in spite of presence of the following prior arts, a technology associated with the bacteriophage for preventing and/or treating infectious diseases by APEC, which is an important problem in breeding birds including poultry, is still insufficient, such that a bacteriophage and a technology associated with the bacteriophage should be developed.

PRIOR ART DOCUMENT

Patent Document (Patent Document 1) U.S. Pat. No. 6,485,902
(Patent Document 2) Korea Patent Registration No. 10-0910961 B 1
(Patent Document 3) Korean Patent Laid-Open Publication No. 10-2009-0021475 A

Non-Patent Document (Non Patent Document 1) Cislo M, et al., Arch. Immunol. Ther. Exp. 2:175-183, 1987
(Non Patent Document 2) Sung Hun Kim et al, Bacteriophage, Novel Alternative Antibiotics, BioWave Vol. 7 Nov. 15, 2005, BRIC

DISCLOSURE

Technical Problem

The present inventors conducted studies in order to solve problems such as resistant bacteria occurring upon the use of antibiotics, and antibiotics remaining in meat, and the like, and efficiently prevent and treat infectious diseases in birds. As a result, the present inventors isolated new bacteriophage ΦCJ23 (KCCM11365P) having a specific bacteriocidal activity against APEC, causing respiratory diseases in poultry, from nature.

In addition, the present inventors identified morphological, biochemical, and genetic characteristics of the novel bacteriophage, and confirmed that the bacteriophage had excellent acid resistance, heat resistance, and the like, thereby developed an antibiotic, a disinfectant, a feed additive, and other compositions using the novel bacteriophage. Further, the present inventors developed a composition for preventing or treating infectious diseases generating in birds, and a method of preventing or treating the disease using the composition.

The present invention provides a novel bacteriophage ΦCJ23 (KCCM11365P) having a specific bactericidal activity against APEC.

In addition, the present invention provides a composition of preventing and/or treating infectious diseases by APEC containing the bacteriophage ΦCJ23 (KCCM11365P) as an active ingredient.

Further, the present invention provides an antibiotic, a feed additive, a drinking water additive, a disinfectant, or a cleaner containing the bacteriophage 410CJ23 (KCCM11365P) as an active ingredient.

Furthermore, the present invention provides a method of preventing and/or treating infectious diseases by APEC using the bacteriophage 410CJ23 (KCCM11365P) or a composition containing the bacteriophage ΦCJ23 (KCCM11365P) as an active ingredient.

Technical Solution

An exemplary embodiment of the present invention provides a novel bacteriophage ΦCJ23 (KCCM11365P) having a specific bactericidal activity against avian pathogenic *Escherichia coli*(APEC).

Another exemplary embodiment of the present invention provides a composition for preventing or treating an infectious disease caused by APEC, containing the bacteriophage ΦCJ23 (KCCM11365P) as described above as an active ingredient.

Another exemplary embodiment of the present invention provides an antibiotic, a feed additive, a drinking water additive, a disinfectant, or a cleaner containing the bacteriophage ΦCJ23 (KCCM11365P) as described above as an active ingredient.

Another exemplary embodiment of the present invention provides a method of preventing or treating an infectious disease caused by APEC, the method including administering the bacteriophage ΦCJ23 (KCCM11365P) or the composition containing the bacteriophage ΦCJ23 as described above as an active ingredient to birds.

Advantageous Effects

The bacteriophage ΦCJ23 (KCCM11365P) according to the present invention has the specific bactericidal activity against avian pathogenic *Escherichia coli*(APEC).

In addition, since the bacteriophage ΦCJ23 (KCCM11365P) of the present invention has excellent acid resistance, heat resistance, and drought resistance, it may not only be used as a material for preventing or treating infectious diseases by APEC in various temperature or pH ranges, but also utilized as an antibiotic, a feed additive, a drinking water additive, a disinfectant, and a cleaner, or the like.

Further, according to the present invention, infectious diseases by APEC may be prevented or treated by administering the bacteriophage ΦCJ23 (KCCM11365P) or a composition containing the bacteriophage ΦCJ23 (KCCM11365P) as an active ingredient to birds.

DESCRIPTION OF DRAWINGS

FIGS. 6A, 6B and 6C are tables showing results of comparing homologues of the genome sequence of the bacteriophage ΦCJ23 and decoded genome sequences of other bacteriophages.

BEST MODE

Figure 1:
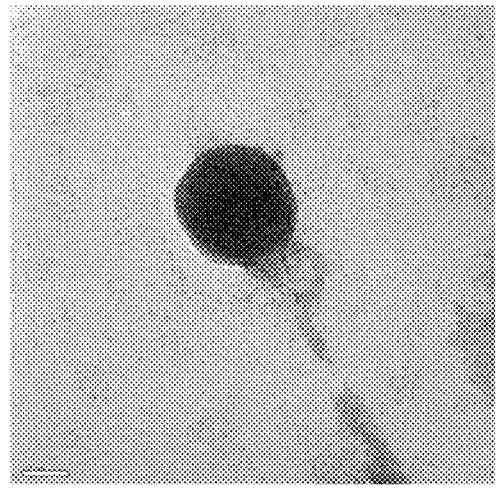
FIG. 1 is an electron microscope photograph of a novel bacteriophage ΦCJ23 (KCCM11365P, hereinafter, referred to as 'ΦCJ23').

Hereinafter, the present invention will be described in detail. Since contents that are not described in the present specification may be sufficiently recognized and inferred by those skilled in the art or similar art, a description thereof will be omitted.

In detail, one embodiment of the present invention provides a novel bacteriophage ΦCJ23 (KCCM11365P) having a specific bacteriocidal activity against avian pathogenic *Escherichia coli*(APEC).

APEC, which is *E. coli* infected through respiratory tract of birds such as, chickens, ducks, turkeys, or the like, infiltrates into bodies of birds through respiratory mucosa to cause various diseases such as septicemia, granuloma, air sacculitis, salpingitis, arthritis, or the like. APEC is a Gram-negative, rod-shaped bacterium similarly to a general *E. coli*, and has motility due to peritrichous flagella, and is an aerobic or facultative anaerobic bacterium decomposing lactose or fructose to produce acid and gas.

APEC well grows in a general medium, and may grow at about 7 to 48° C., and an optimal growth temperature is about 35 to 37° C. Particularly, virulence factors are effectively expressed at about 42° C., which is close to a body temperature of the bird. In addition, APEC may grow in a pH range of 4.5 to 9.0.

A bacteriophage is a bacteria-specific virus infecting specific bacteria to suppress and inhibit growth of the bacteria, and means a virus including single or double stranded deoxyribonucleic acid (DNA) or ribonucleic acid (RNA) as a genetic material.

The bacteriophage ΦCJ23 of the present invention, which is a species-selective bacteriophage that selectively infects APEC, has a structure of an isometric capsid but a tail is not observed (FIG. 1), and morphologically belongs to Podoviridae.

The following microorganism has been deposited in accordance with the terms of the Budapest Treaty with the Korean Culture Center of Microorganisms (361-221, Hongjedong, Seodamun-gu, Seoul, Korea, on the date indicated:

| Microorganism | Accession No. | Date of Deposit |
| --- | --- | --- |
| Bacteriophage ΦCJ23 | KCCM11365P | Jan. 30, 2013 |

The bacteriophage ΦCJ23, which was newly isolated by the present inventors, was deposited at Korean Culture Center of Microorganisms (361-221, Hongjedong, Seodamun-gu, Seoul, Korea), as deposition number KCCM11365P on Jan. 30, 2013. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from the date of deposit. The deposit will be made available by CNCM under the terms of the Budapest Treaty, and subject to an agreement between Applicant and CNCM which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strains is not to be construed as a license to practice the invention in contravention of the rights granted under the authority of any government in accordance with its patent laws.

In another embodiment, the present invention provides a composition for prevention or treating infectious diseases by APEC containing the bacteriophage ΦCJ23 as an active ingredient.

Since the bacteriophage ΦCJ23 has an antibacterial activity capable of specifically killing APEC, it may be used to prevent or treat diseases generated by infection of APEC. As a preferable example of the infectious diseases by APEC, there is avian colibacillosis, but the present invention is not limited thereto.

The avian colibacillosis, which is a disease generated when the respiratory track of birds, or the like, is infected by pathogenic *E. coli*, causes various lesions such as airsacculitis, perihepatitis, peritonitis, pericarditis, salpingitis, omphalitis, osteomyelitis, or septicemia, or the like, thereby inhibits growth and causes mortality of the infected birds.

The term "prevention" as used herein, refers to all actions of providing the bacteriophage ΦCJ23 and/or the composition comprising the bacteriophage ΦCJ23 as the active ingredient to targets, to suppress the corresponding disease or retard disease occurring.

The term "treatment" as used herein, refers to all actions of providing the bacteriophage ΦCJ23 and/or the composition comprising the bacteriophage ΦCJ23 as the active ingredient to targets, to thereby allow the symptom of the corresponding disease caused by infection to get better or to be alleviated.

The composition for preventing or treating the infectious disease caused by APEC according to the present invention may contain the bacteriophage ΦCJ23 in an amount of preferably $5 \times 10^2$ to $5 \times 10^{12}$ pfu/14, more preferably, $1 \times 10^6$ to $1 \times 10^{10}$ pfu/ml.

The composition for preventing or treating the infectious disease caused by APEC according to the present invention may further contain a pharmaceutically acceptable carrier, and be formulated together with the carrier to be provided as food, a feed additive, a drug, or a drinking water additive, etc. The term "pharmaceutically acceptable carrier" as used herein, means a carrier or a diluent that does not stimulate living organism nor inhibit biological activity and properties of an administered compound.

A kind of carrier usable in the present invention is not particularly limited, and any carrier may be used as long as it is generally used in the art and is pharmaceutically acceptable. As a non-restrictive example of the carrier, there are saline, sterile water, Ringer's solution, buffered saline, an albumin injection solution, a dextrose solution, a maltodextrin solution, glycerol, ethanol, and the like. These may be used alone or as a mixture of at least two of these.

In addition, if necessary, another general additive such as an antioxidant, a buffer, and/or a bacteriostatic agent, etc., may be further added and be used, and the composition may be formulated into a formulation for injection such as an aqueous solution, suspension, emulsion, or the like, pills, capsules, granules, tablets, or the like by additionally adding a diluent, a dispersant, a surfactant, a binder, and/or a lubricant, etc., and then be used.

An administration method of the composition for preventing or treating infectious diseases by APEC of the invention is not particularly limited, but any method generally used in the art may be used. As a non-restrictive example of the administration method, the composition may be orally or parenterally administered.

As a non-restrictive example of the formulation for oral administration, there are troches, lozenge, tablets, aqueous suspensions, oily suspensions, prepared powder, granules, emulsions, hard capsules, soft capsules, syrups, or elixirs, etc.

In order to formulate the composition according to the present invention into a formulation such as a tablet, or a capsule, etc., the formulation may further contain a binder such as lactose, saccharose, sorbitol, mannitol, starch, amylopectin, cellulose, or gelatin; an excipient such as dicalcium phosphate, or the like; a disintegrant such as corn starch, or sweet potato starch, or the like; a lubricant such as magnesium stearate, calcium stearate, sodium stearyl fumarate, polyethylene glycol wax, or the like. In the case of the capsule formulation, the formulation may further contain a liquid carrier such as fatty oil in addition to the above-mentioned materials.

As a parenteral administration method of the invention, an intravenous administration method, an abdominal administration method, an intramuscular administration method, a subcutaneous administration method, or a local administration method, etc., may be used. In addition, a method of applying or spraying the composition onto a disease site may also be used, but the present invention is not limited thereto.

An example of the formulation for the parenteral administration may include formulations for injection such as subcutaneous injection, intravenous injection, intramuscular injection, or the like; suppository formulations; or spray formulations such as aerosol formulations capable of being inhaled through respiratory track, or the like, but the present invention is not limited thereto. In order to formulate the composition into the injection formulation, the composition according to the present invention may be mixed with a stabilizer or a buffer in water to thereby prepare a solution or suspension, and then, the prepared solution or suspension may be formulated in a unit dose for an ampoule or vial. In the case of formulating the composition into the spray formulation such as the aerosol formulation, or the like, a propellant, or the like, may be mixed together with an additive so that a water-dispersed condensate or wet powder could be dispersed.

A suitable application, spray, or administration dose of the composition in the invention for preventing or treating infectious diseases by APEC may be variously determined depending on factors such as age, weight, sex, degree of symptom of disease, ingesting food, excretion rate of administration subject animals, as well as a method of formulating the composition, an administration method, an administration time and/or route. Generally, a veterinarian having ordinary skill in the art may easily determine and prescribe an effective dose for the desired treatment.

In another embodiment, the present invention provides an antibiotic comprising the bacteriophage ΦCJ23 as an active ingredient.

The term "antibiotic" as used herein, means an agent capable of being provided to subjects including humans in a drug form to thereby kill bacteria, and corresponds to a concept collectively indicating a preservative, a disinfectant, and an antibacterial agent.

The antibiotic containing the bacteriophage ΦCJ23 according to the present invention as the active ingredient, may be advantageous as having high specificity to APEC as compared to conventional antibiotic, thereby not killing beneficial bacteria but killing specific pathogenic bacterial, and does not induce drug resistance, so that the antibiotic according to the present invention may be provided as a novel antibiotic having an elongated lifespan as compared to conventional antibiotic.

In another embodiment, the present invention provides a feed additive and a drinking water additive for birds, particularly, poultry containing the bacteriophage ΦCJ23 (KCCM11365P) as an active ingredient.

The term "poultry" as used herein, is a concept collectively indicating animals belonging to birds among domestic animals. The poultry is not particularly limited, but may include, preferably, at least one selected from a groups consisting of chickens, ducks, and turkeys.

The feed additive or the drinking water additive for birds according to the present invention may be used in a manner in which the bacteriophage ΦCJ23 or the composition containing the same is individually prepared in a feed additive or drinking water additive form, and then mixed with a feed or drinking water, or in a manner in which the bacteriophage ΦCJ23 or the composition containing the same may be directly added at the time of preparing the feed or the drinking water.

The bacteriophage ΦCJ23 or the composition containing the same used as the feed additive or drinking water additive according to the present invention, may be in a liquid state or dried state, and preferably, in a dried powder form.

A drying method for preparing the feed additive and the drinking water additive according to the present invention in the dried powder form is not particularly limited, but a method generally used in the art may be used. As a non-restrictive example of the drying method, there are an air drying method, natural drying method, a spray drying method, a freeze-drying method, or the like. These methods may be used alone or at least two methods may be used together with each other.

Another non-pathogenic microbe may be additionally added to the feed additive or drinking water additive of the invention. A non-restrictive example of the microbe capable of being added may be selected from a group consisting of *Bacillus subtilis*, capable of producing protease, lipase, and/or sugar converting enzyme such as *Bacillus subtilis*, or the like; *Lactobacillus* sp. having physiological activity and degradation activity for an organic material under anaerobic conditions such as cow's stomach; mold fungi having effects of increasing weight of domestic animal, milk yield, and digestibility of the feed such as *Aspergillus oryzae*, or the like; and yeasts such as *Saccharomyce scerevisiae*, or the like. These may be used alone or as a mixture of at least two of these.

The feed additive or the drinking water additive containing the bacteriophage 410CJ23 according to the present invention as the active ingredient may further contain other additives, as needed. As a non-restrictive example of the usable additive, there are a binder, an emulsifier, a preservative, and the like, which are added in order to prevent quality of the feed or drinking water from being deteriorated; amino acids, vitamins, enzymes, probiotics, flavoring agents, non-protein nitrogen compounds, silicates, buffers, coloring agents, extractants, or oligosaccharides, and the like, which are added in order to increase utility of the feed or drinking water. Otherwise, the additive may further include a feed mixing agent, or the like. These may be used alone or as a mixture of at least two of these.

The feed additive may be contained at a content of 0.05 to 10, more preferably 0.1 to 2 parts by weight based on 100 parts by weight of the feed. The drinking water additive of the invention may be contained at a content of 0.0001 to 0.01, more preferably 0.001 to 0.005 parts by weight based on 100 parts by weight of the drinking water. The activity of the bacteriophage ΦCJ23 against APEC may be sufficiently exhibited in the above-mentioned range.

In another embodiment, the present invention provides a feed or drinking water prepared by adding a feed additive or a drinking water additive containing the bacteriophage ΦCJ23 as an active ingredient or directly adding the bacteriophage ΦCJ23.

The feed used in the present invention is not particularly limited, but any feed generally used in the art may be used. A non-restrictive example of the feed may include plant feeds such as grains, roots and fruit, food processing byproducts, algaes, fiber, pharmaceutical byproducts, fats, starches, cucurbitaceous, or grain byproducts; and animal feeds such as proteins, inorganic materials, fats, minerals, single cell proteins, animal planktons, or foods. These may be used alone or as a mixture of at least two of these.

The drinking water used in the present invention is not particularly limited, but any drinking water generally used in the present invention may be used.

In another embodiment, the present invention may provide a disinfectant or a cleaner containing the bacteriophage ΦCJ23 as an active ingredient. A formulation of the disinfectant or cleaner is not particularly limited, it may be formulated into any formulation known in the art.

The disinfectant may be sprayed in order to remove APEC, and can be sprayed onto a region in which birds live, a slaughterhouse, a mortality area, a cooking place or cooking equipment, or the like, but the present invention is not limited thereto.

The cleaner may be used to wash surface of the skin or each of the sites of bodies of birds exposed or to be exposed to APEC, but the present invention is not limited thereto.

In another embodiment, the present invention provides a method of preventing or treating infectious diseases by APEC by using the bacteriophage ΦCJ23 or the composition comprising the same as an active ingredient.

In detail, the method of preventing or treating infectious diseases according to the present invention, may include administering the bacteriophage ΦCJ23 or the composition containing the same as the active ingredient to birds infected by APEC or being at risk of infection of APEC in a pharmaceutically effective dose. It will be apparent to those skilled in the art that when the pharmaceutical composition is administered to patient, the suitable total daily dose may be determined by an attending physician or veterinarian within the scope of sound medical judgement.

A specific pharmaceutically effective dose of the bacteriophage ΦCJ23 or the composition containing the same as the active ingredient for a specific bird, may be determined considering an administration time and an administration route of the bacteriophage ΦCJ23 or the composition containing the same, a secretion rate of the composition, a therapy duration period, or the like, in addition to a kind and a degree of the desired response, age, weight, general healthy state, sex, or diet of the corresponding individual. In addition, the pharmaceutically effective dose may be variously changed according to various factors such as ingredients of drugs or other compositions simultaneously or separately used and similar factors well known in a medical field.

The bacteriophage ΦCJ23 according to the present invention or the composition containing the same as the active ingredient may be administered as a pharmaceutical form (nasal spray) to birds or administered in a method of directly added to a feed or drinking water of the birds and then feeding the feed or drinking water. In addition, the bacteriophage ΦCJ23 or the composition containing the same may be mixed in a feed or drinking water in a form of a feed additive or drinking water additive and then administered.

The administration route and administration method of the bacteriophage ΦCJ23 according to the present invention or the composition containing the same as the active ingredient are not particularly limited, but any administration route and administration method may be used as long as the bacteriophage ΦCJ23 or the composition containing the same may arrive at the corresponding target tissue. That is, the bacteriophage ΦCJ23 or the composition containing the same as the active ingredient may be administered through various oral or parenteral routes. Non-restrictive example of the administration route, oral, rectal, local, intravenous, intraperitoneal, intramuscular, intraarterial, subcutaneous, and nasal administration, or inhalation, etc., may be performed.

Hereinafter, the present invention will be described in detail through the Examples. However, these Examples are only to illustrate the present invention, and a scope of the present invention is not limited to these Examples.

[Example 1] Isolation of Bacteriophage Being Infected By APEC

Examples 1-1

Screening of Bacteriophage and Isolation of Single Bacteriophage

After 50 ml of a sample obtained from feces and environmental samples from areas of a duck farm in Boryeng, South Chungchong Province was centrifuged at 4,000 rpm for 10 minutes, the supernatant was filtered with a 0.45 μm filter to prepare a sample solution, and then a soft agar overlay method was performed using the prepared sample solution. The soft agar overlay method is a method of observing a lytic action of bacteriophage using host cells growing in top agar (attached onto a solid medium using 0.7% agar).

In detail, 1810 of sample filtrates was mixed with 150 μl of a shake culture solution ($OD_{600}$=2) of APEC(E10-4) obtained from College of Veterinary Medicine in Kunkuk University and 2 ml of 10×LB medium (tryptone 10 g/l; yeast extract 5 g/l; and NaCl 10 g/l) and cultured at 37° C. for 18 hours. Then, the culture solution was centrifuged at 4,000 rpm for 10 minutes, and the supernatant was filtered using the 0.45 μm filter. Then, after a mixed solution of 3 ml of 0.7% (w/v) agar and 150 μl of the shake culture solution ($OD_{600}$=2) of APEC(E10-4) was poured and hardened on to a LB plate medium, 100 of the sample solution was dropped thereon, followed by culturing at 37° C. for 18 hours. Then, it was confirmed that a plaque was formed.

Since it is known that one kind of bacteriophage is present in a single plaque, a single bacteriophage was intended to be isolated from the formed plaque. In detail, the plaque was added to 400 μl of a SM solution (NaCl 5.8 g/l; $MgSO_4 7H_2O$ 2 g/l; 1M Tris-Cl (pH 7.5) 50 ml) and left at room temperature for 4 hours, thereby obtaining a bacteriophage solution.

Thereafter, 100 μl of the bacteriophage solution was mixed with 12 ml of 0.7% (w/v) agar and 500 μl of the shake culture solution ($OD_{600}$=2) of APEC(E10-4), followed by performing the soft agar over lay method using a LB plate medium having a diameter of 150 mm. The culturing was performed until APEC was completely lysed. After the culturing was terminated, 15 ml of the SM solution was added to the LB plate medium and left at room temperature for 4 hours, thereby obtaining a bacteriophage solution.

After the solution was recovered and 1% (v/v) chloroform was added thereto, the mixture was mixed for 10 minutes, followed by centrifugation at 4,000 rpm for 10 minutes, thereby obtaining a supernatant. The obtained supernatant was filtered with a 0.45 μm filter, thereby obtaining a final sample.

Examples 1-2

Large-Scale Culture and Purification of Bacteriophage

The bacteriophage obtained in Example 1-1 was cultured at large scale using APEC (E10-4), and then the bacteriophage was purified therefrom.

In detail, after APEC (E10-4) was shake-cultured, an aliquot of $1.5 \times 10^{10}$ cfu was centrifuged at 4000 rpm for 10 minutes and then resuspended in 4 TO of the SM solution. The bacteriophage of $1.5 \times 10^6$ pfu was inoculated thereto (multiplicity of infection(MOI)=0.0001), and left at room temperature for 20 minutes.

Thereafter, the solution was inoculated into 150 ml of the LB medium and cultured at 37° C. for 6 hours. After the culturing was terminated, chloroform was added at an amount of 1% (v/v) of a final volume and stirred for 20 minutes. Then, restriction enzymes DNase I and RNase A were added so as to have a final concentration of 1 μg/ml, respectively, and the solution was left at 30° C. for 30 minutes. Then, NaCl and polyethylene glycol (PEG) were added so as to have final concentrations of 1M and 10% (w/v), respectively, and further left at 4° C. for 3 hours, followed by centrifugation at 4° C. and 12,000 rpm for 20 minutes, thereby obtaining precipitates.

The obtained precipitate was suspended in 5 μl of SM solution and left at room temperature for 20 minutes. Then, 4 ml of chloroform was added thereto and stirred, followed by centrifugation at 4° C. and 4,000 rpm for 20 minutes, thereby obtaining a supernatant. Thereafter, the supernatant was filtered with a 0.45 μm filter, and ultracentrifugation (35,000 rpm, 1 hour, 4° C.) using a glycerol density gradient method (density: 40%, 5% glycerol) was performed, thereby purifying the bacteriophage.

The present inventors designated the bacteriophage obtained by extracting the sample from the feces sample of the farm and having the specific bacteriocidal activity against APEC as "Bacteriophage ΦCJ23" and deposited the bacteriophage at Korean Culture Center of Microorganisms (361-221, Hongj edong, Seodaemun-gu, Seoul, Korea) under deposition number KCCM11365P on Jan. 30, 2013.

Example 2

Examination on ΦCJ23 Infection of APEC

In order to confirm whether or not the bacteriophage ΦCJ23 purified in Example 1 has a lytic activity on *E. coli* strains other than APEC(E10-4), cross infection with other *E. coli* species was performed.

In detail, among wild-type *E. coli* strains obtained from College of Veterinary Medicine in Kunkuk University, two kinds of APEC strains(E10-4 and E09-35) and six kinds of non-pathogenic *E. coli* strains(E09-1, E09-10, E09-13, E09-14, E09-15, and E09-16) were cultured, respectively, thereby obtaining culture solutions. Each of the culture solutions and the purified ΦCJ23 were used to perform the soft agar overlay method, and whether or not a plaque was formed was confirmed.

The results were shown in the following Table 1.

TABLE 1

| Strain name | Plaque formation |
|---|---|
| APEC (E10-4) | ○ |
| APEC (E09-35) | ○ |
| *E. coli* (E09-1) | X |
| *E. coli* (E09-10) | X |
| *E. coli* (E09-13) | X |
| *E. coli* (E09-14) | X |
| *E. coli* (E09-15) | X |
| *E. coli* (E09-16) | X |

As shown in Table 1, it may be appreciated that the bacteriophage ΦCJ23 purified in Example 1 did not have the lytic activity on the non-pathogenic *E. coli* strains.

Example 3

Observation of Morphology of ΦCJ23

The bacteriophage ΦCJ23 purified in Example 1 was diluted in a 0.01% gelatin solution, and then fixed in a 2.5% glutaraldehyde solution. The fixed bacteriophage was dropped onto a carbon-coated mica plate (ca. 2.5 mm×2.5 mm), adapted thereto for 10 minutes, and washed with sterile distilled water.

A carbon film was mounted on a copper grid, stained with 4% uranyl acetate for 30 to 60 seconds, dried, and investigated using a transmission electron microscope (JEM-1011, 80 kV, magnification×120,000 to ×200,000) (FIG. 1).

FIG. 1 is an electron microscopy photograph of the bacteriophage ΦCJ23. It was judged that the bacteriophage ΦCJ23 has a morphotype with icosahedral head of a size about 40 nm without a tail, such that it morphologically belongs to Podoviridae.

Example 4

Genomic DNA Size Analysis of ΦCJ23

Genomic DNA was extracted from the bacteriophage ΦCJ23 purified in Example 1.

In detail, 20 mM Ethylenediaminetetraacetic acid (EDTA), 50 μg/ml proteinase K, and 0.5% (w/v) sodium dodecyl sulfate (SDS) were added to a culture solution of the purified bacteriophage ΦCJ23, and left at 50° C. for 1 hour. Then, an equal volume of phenol (pH 8.0) was added and stirred, followed by centrifugation at room temperature and 12,000 rpm for 10 minutes, thereby obtaining a supernatant.

The supernatant was mixed with an equal volume of PC (phenol:chloroform=1:1) and centrifuged at room temperature and 12,000 rpm for 10 minutes, thereby obtaining a supernatant. The supernatant was mixed with an equal volume of chloroform and centrifuged at room temperature and 12,000 rpm for 10 minutes, thereby obtaining a supernatant. The obtained supernatant was sequentially mixed with of 3M sodium acetate to be 10% (v/v) of total volume and a double volume of cold 95% ethanol, and left at −20° C. for 1 hour.

Subsequently, centrifugation was performed at 0° C. and 12,000 rpm for 10 minutes, and the precipitate was obtained by removing the supernatant. Then, 500 of Tris-EDTA (TE) buffer (pH 8.0) was added thereto to dissolve the obtained precipitate. The extracted DNA was diluted 10 times, and a concentration was measured by measuring absorbance at $OD_{260}$.

Figure 2:
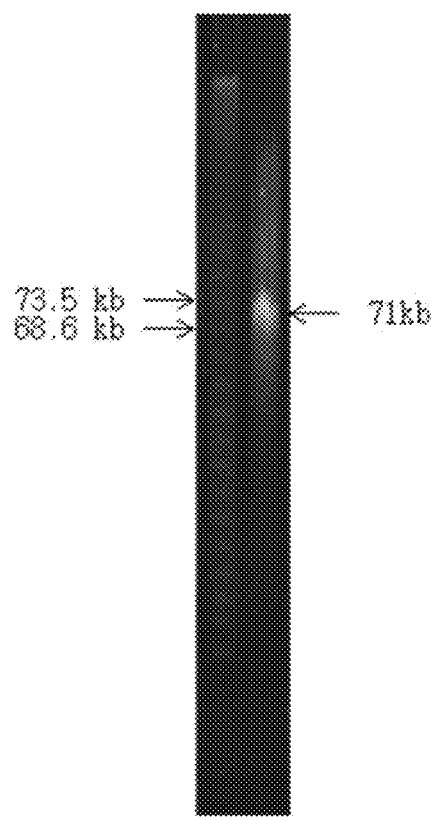
FIG. 2 shows a pulsed field gel electrophoresis (PFGE) result of the novel bacteriophage ΦCJ23.

Next, 1 μg of DNA was loaded onto 1% pulse-field gel electrophoresis (PFGE) agarose gel, and for 20 hours using a BIORAD PFGE system program 7 (size range: 25-100 kb; switch time ramp: 0.4-2.0 seconds, linear shape; forward voltage: 180 V; reverse voltage: 120 V) (FIG. 2).

FIG. 2 is a pulsed field gel electrophoresis (PFGE) photograph of the genomic DNA of the bacteriophage ΦCJ23, and it may be confirmed that the genomic DNA of the bacteriophage ΦCJ23 has a size of about 71 kbp.

Example 5

Protein Pattern Analysis of ΦCJ23

150 μl of purified bacteriophage ΦCJ23 solution at a titer of $10^{10}$ pfu/ml, was mixed with 3 μl of a 5×SDS sample solution, and heated for 5 minutes. Then, the 15% SDS-PAGE was performed (FIG. 3).

Figure 3:
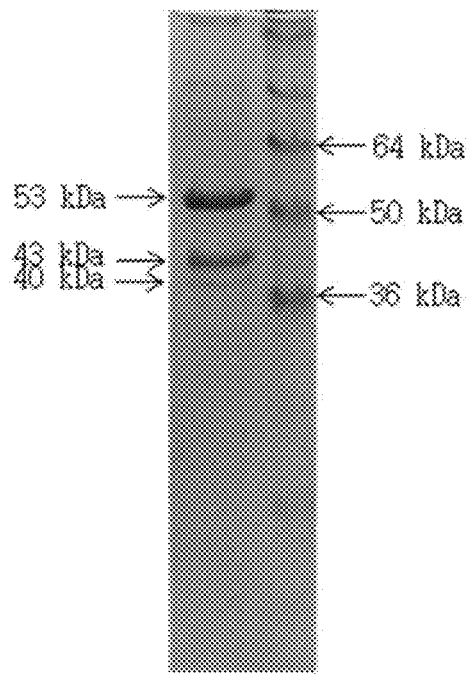
FIG. 3 shows a sodiumdodecylsulfate-polyacrylamide gel electrophoresis (SDS-PAGE) result of the novel bacteriophage ΦCJ23.

FIG. 3 is an electrophoresis photograph showing a result of SDS-PAGE performed on the bacteriophage ΦCJ23, and main proteins having sizes of about 40 kDa, 43 kDa, and 53 kDa were observed.

Example 6

Genetic Characteristics Analysis of ΦCJ23

In order to confirm genetic characteristics of the bacteriophage ΦCJ23 purified in Example 1, DNA of the bacteriophage ΦCJ23 was analyzed using a FLX titanium sequencer (Roche), which is a gene analysis apparatus. The genes were assembled at Macrogen Inc. using GS and de novo assembler software (Roche). Sequence analysis of an open reading frame was performed using GeneMArk.hmm, Glimmer v3.02, and FGENESB software. Identification of the open reading frame was performed using BLASTP and InterProScan program.

The genome sequence of the bacteriophage had various similarities with that of the existing reported bacteriophage, but it was confirmed that there was no bacteriophage of which all of the fractions were completely (100%) equal. Therefore, it may be confirmed that the bacteriophage was a newly isolated bacteriophage.

FIGS. 6A, 6B and 6C show results obtained by comparing homologues of the genome sequence of the bacteriophage ΦCJ23 and decoded genome sequences of other bacteriophages.

Example 7

Stability test of ΦCJ23 Depending on pH

In order to confirm whether or not the bacteriophage ΦCJ23 may have stability in a low pH environment in stomach, stability test was performed over a wide pH range (pH 2.1, 2.5, 3.0, 3.5, 4.0, 5.5, 6.4, 7.5, 8.3, 9.2 and 11.0)

For test, various pH solutions (sodium acetate buffer (pH 2.1, pH 4.0, pH 5.5, and pH 6.4), sodium citrate buffer (pH 2.5, pH 3.0, and pH 3.5), sodium phosphate buffer (pH 6.9 and pH 7.4), and Tris-HCl solution (pH 8.2, pH 9.0, pH 9.8, and pH 11.0)) were prepared at a concentration of 0.2 M, respectively.

After 900 of each of the pH solutions was mixed with 100 of bacteriophage solution having a titer of 2.0×1010 pfu/ml so that a concentration of each of pH solution became 1M, each of the pH solutions was left at room temperature for 2 hours. In a control group, 20 μl of the bacteriophage solution (2.0×1010 pfu/ml) was mixed with 180 μl of SM solution and then left at room temperature for 2 hours. Then, the reaction solution was diluted step by step, and 10 μl of each of the diluted solutions was dropped and cultured at 37° C. for 18 hours by a soft agar overlay method, and the titer was measured through the presence or absence of lysis.

Figure 4:
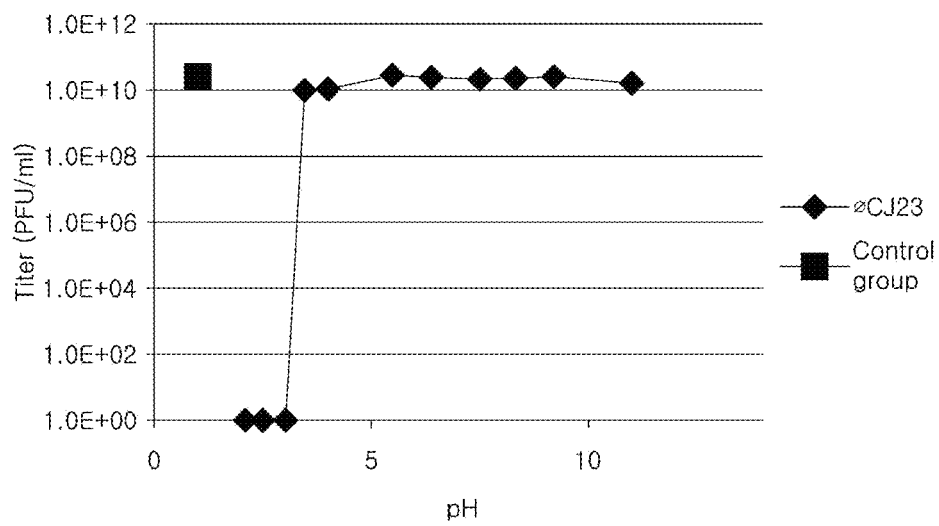
FIG. 4 is a graph showing a result of an acid resistance test of the novel bacteriophage ΦCJ23.

FIG. 4 shows a result of the acid resistance test of the bacteriophage ΦCJ23. As shown in FIG. 4, it may be confirmed that the bacteriophage ΦCJ23 did not lose its activity and was stable in a pH range of 3.5 to 11.0 as compared to the control group.

Example 8

Stability Test of ΦCJ23 Depending on Temperature

A test for confirming stability against heat generated during a formulating process of the bacteriophage in the case of using the bacteriophage as a feed additive formulation among formulations of the bacteriophage was performed.

Figure 5:
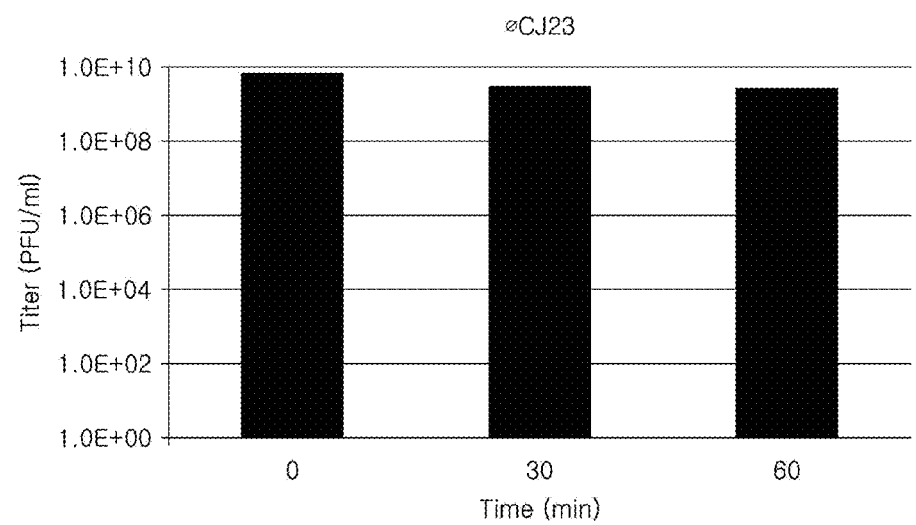
FIG. 5 is a graph showing a result of a heat resistance test of the novel bacteriophage ΦCJ23.

In detail, 100 µl of the bacteriophage ΦCJ23 solution having a concentration of 6.5×10⁹ pfu/ml was left at 60° C. for 30 minutes, and then the solutions above were diluted step by step. 10 µl of the diluted solutions at each step was dropped and cultured at 37° C. for 18 hours by a soft agar overlay method, and the titer was measured through the presence or absence of lysis (FIG. 5).

FIG. 5 shows a result of a heat resistance test of the bacteriophage ΦCJ23. As shown in FIG. 5, the titer of the bacteriophage ΦCJ23 was not decreased by about 1 log value or more at the time of being exposed at 60° C. for 1 hour.

Example 9

Infection Spectrum Test of ΦCJ23 on Wild-Type Strains of APEC

Whether or not the bacteriophage ΦCJ23 had a lytic activity was tested on 6 wild-type strains of APEC isolated by College of Veterinary Medicine, Kunkuk University other than APEC (E10-4) used in the experiment.

In detail, 10 µl of bacteriophage ΦCJ23 solution having a titer of 10⁸ pfu/ml and mixed with 150 µl of a shake culture solution (OD$_{600}$=2) of each of the strains was dropped and cultured at 37° C. for 18 hours by a soft agar overlay method. Then, whether or not a plaque was formed was observed.

The results were shown in the following Table 3.

TABLE 3

| Strain name | Plaque formation |
|---|---|
| APEC (E09-6) | ○ |
| APEC (E09-11) | ○ |
| APEC (E09-35) | ○ |
| APEC (E10-03) | ○ |
| APEC (E10-04) | ○ |
| APEC (E10-05) | ○ |

As shown in Table 2, it may be confirmed that the bacteriophage ΦCJ23 had effective infectivity on APEC (including O-78 serotype), which is a bacterium causing avian colibacillosis in general poultry farms. Meanwhile, it is known that the O-78 serotype APEC is a strain most frequently found in APEC strains isolated in the general poultry farms.

The invention claimed is:

1. A composition comprising a bacteriophage ΦCJ23 (KCCM11365P) and an effective amount of a binder sufficient to reduce deterioration of the bacteriophage, wherein the composition is in a dried state.

2. The composition of claim 1, further comprising a pharmaceutically acceptable carrier.

3. The composition of claim 1, wherein the dried state is a dried powder state.

4. The composition of claim 1, wherein the composition is formulated in pills, capsules, granules, or tablets.

5. The composition of claim 1, wherein the binder is at least one selected from the group consisting of lactose, saccharose, sorbitol, mannitol, starch, amylopectin, cellulose, and gelatin.

6. The composition of claim 1, wherein the composition is an additive for adding to an animal feed or drinking water.

7. A method of making an animal feed, the method comprising:
providing a feed material; and
mixing the composition of claim 1 with the feed material to make the animal feed.

* * * * *

SEQUENCE LISTING

```
<160> NUMBER OF SEQ ID NOS: 3

<210> SEQ ID NO 1
<211> LENGTH: 60125
<212> TYPE: DNA
<213> ORGANISM: Artificial Sequence
<220> FEATURE:
<223> OTHER INFORMATION: A part of DNA of  novel bacteriophage CJ23
      Contig00001; Synthetic

<400> SEQUENCE: 1
tatcatcaac tattggagct atcatcatga ctactcaagc tactgtacgt atgaccgcag      60
gaactttact tggtactgtt aactcagctg ctactactgt tgcagatacc ttcggtacag     120
caactaaagc agtaggtatg cttaattcat atgtaagtac tatggcagag aaacaagcca     180
ttcgtactaa attagaaatg catacctttg ttaataaact ggcagaggaa acagctatga     240
ctgagactct gcgtaagaaa agtatcgagg aattctgcaa ggattcagag aacgctcgaa     300
tctataacgc agaatattct aaagtaattg acatcctgac taaagactaa gtcatctagg     360
agactcttcg gagtctcctg ttttgaacat tagatagata gtcaaaagta gataactatc     420
tactttactt ctacttctaa aaaccaagac gctccgcgtc ttatggatga tgtaaatgca     480
tccactaatc attgaacttt tatccttttg tttgggtgtt ctctccgacg agttcacccg     540
taaatcacat aaatctggag agtacaaaat gtctattcaa aaattcactt tcggtcaatc     600
taacgctgct gcttctactg ctaaaactga caaaccaaaa gctcagttct ggctgaacat     660
tggttatgta gctaacgaag gctctgatga tgagaaattc atctctctgc ctactggtat     720
tccactggat actcaggagc cactgcctac taatagcagc aatgctgact tccgtgctat     780
gcgttgtgca cagaacgact tgctggaaca gttaattgag tatgctcaga acctggaacc     840
aggtgaagaa ggtatcataa acctgcaagt tcaacttcgt cgtgtgaaag cagaggctgc     900
tgacatccca gcagacgaga ataaatatgc tcgtaaactg actttctaat caaccaatag     960
actcccttcg gggagtcttt tatttttaac tagacgataa gctatttcta cttttttgagt    1020 atctttagac gaagggtact gaaacagtaa ccagatagat atagatttat attagaagag    1080
```

```
gaattaacca tgttagattt catcgctttc tgtgtaatct tctactttct gggttggaag    1140
ttacgtcata aatggttgct tattgctaaa ctgccattcg ttactatcga gtgtctcatt    1200
gctagtatta aacacaagaa agcaatgact cagtactaca agcaacaagc agaagagttt    1260
gcaaagagga accagtgata ttcactaaca tagatgatgc cattgaagaa tgtatctttc    1320
gtaggtatca cactggtgta cagaaacgac actatggtgt tgtacaactc aatggctatc    1380
aaatggttgt aagaattgta cgtaagaata aaccttttaa ctttatgtgg agtactaaat    1440
catgcgtaaa tcattaatca tgggaaccag agaagacgtg caaagatga aagaacgtct     1500 ggttgctaag aaacagacgt ctgaaccagt acgtaagatt gttaccttca accattcatg    1560
tatcaagtaa ctaggagtcc tccattagga gggcttctat tttttattcc tgaatagtta    1620
gatatgtatt taaataggag aaataacctt gaatgaaatt gtttgtatac ttcctcaatc    1680
agctaagata gctgacagga atatccgtat ccacttaccc tttccattaa gtaatccatt    1740
cactcgtaat gaaagaacca cagtagaaga tgtagaggta gcttatgaag cttacctccg    1800
taatcgtctt attagtgggg acaaactaat tacagcagag atggaaagga ttgcatcctt    1860
tgtaacagat agtacaggca agcctgttgg cttaattggt acagagtctg atgttaacgt    1920
tattcgtaaa atattaatgg aggcattaaa tggctaaata aaggtaata cgctttgcag     1980 ataatgaacg tggtattggt gcagaagtag agaaaaaaac attctttgga accagtacat    2040
gggtaaaagt tagtacacat ggacacagtg agtgcttcga taaatgggtt aataaagaaa    2100
ccggtgtatc cggttatgct gatactaccc aatcagagat taatgacttc tatactgcca    2160
atcacattac taaggaataa acaaaatgtt gttcagcact aattatggta tttgcccaat    2220
ttgcaataaa ggaagaggag ttgctaatca taagaagtgt agtcgtatat tacagaaaca    2280
acggaatcag aaagaatggg ataaggtgct aaataatcag cataaagaag agaatcaaca    2340
gatggctgtt aaagcatcta ctcaacgtat tcgccgtatt aactatatac aggggtatca    2400
gaaatgatta ttgcatatcc tacaggcaag actgtggaat atatgaagca tactattcaa    2460
gtgcctcact gggttaagta tatagcatta ctacctcgtc aatataagag tgctaatacc    2520
tcactaatag gattctctaa aaaacctaag ctaacagaaa acaatatctg ggtatcctct    2580
gggagacaag aagagattgg tttttgtgat ttgagtattg tcaataataa cgtttaccta    2640
acgctggaga aagtagcatg aatattgaaa attatgaaat cactttagta acagcagaca    2700
gtaaaactgt gattaacaaa caattaaata atgaccctga gatgcttaac tgggttgcag    2760
agcaatttgc tgatgttaac tcagcacagg taaccctacg gaatatgtca ggaaaagtag    2820
tagcatttac aggcaaggag ccagtatgaa aactattcta gtaatccatg attctacgtt    2880
tactgatgta gataagatga tgcgtaatat tgattatgta tctcagacaa gccaagcatt    2940
caatgaagag tttactctgt actgcaatgc tgaatctcct ctggttccta tccttaagga    3000
atcaggtcta ccattctcta cagagaactt cccggaagaa ccagactatg taatctcatt    3060
tatctatgac ttacatgatg gttctgaaac tagtgaatta gctatgaacc agtggcgtag    3120
taaacgtcct gtgtttgcat ttcaggtact taaaccatga agattatgtc attaggtgat    3180
gacaccaatg ctttacttgg tgtatctgca cgtccaatta tcattgttaa taaacatcac    3240
ggtaaatccg gtgagtatat tgggcgtggc tcaccattag gcaatccatt cgtcattggt    3300
aaacatggaa ccagagagca agtaattgct aagtataaag tctggttaca agaacagatt    3360
gataaaggta atccagttgt actggatgaa cttaatcgtc tgggtaataa agccattgat    3420
gagaaaggat tagccttaca gtgcttctgt tatccaaaac catgtcatgg tgaggttatt    3480
```

```
aaagagaagc tagtaaaggc tatgtataac tactttgtag aaaatctaaa aggataattt    3540
atgaaagaaa tcttagtatt cactactaat gtacttggac agcataacaa tgctgctgcc    3600
aaattagctt ataagaaaca cggtgctcgc tggggcatgg cctatggtca ttatggtaat    3660
agctttgcca ttccagtaaa ggatggttat ggtaaccgta ttaaagaagg tgctatctat    3720
ggcttcattg aaggctttat tgcatatgca tcttctaatc cacaatggga tttcaaagta    3780
atgggagata actttctgga cccataccty ttcaataatg tcactggcaa tgtgctattg    3840
ccagaagcat ggcataaata cttaggtaat gcttacaact attggagtta ataatgactt    3900
atgaagaact atggtctgct caagtcagag ccagagcact cacacgacac gatatctatt    3960
gtgcattaca aacgaattaa agagtcgta ctaagctggg tcacatatcc ggcttagtta     4020
aaatatctat gactagccta gtctggcctt atcagaagaa aagtaatgag tttaatggta    4080
atggtctgca tgtacgcatc gactacatcg gtaatgaaaa cagtattcgt attaccttt     4140 ggactaagcg ttagttaatg gctgctccgc agcttttggt tattaatcac atttaggaga    4200
ataagcgatg tactcatcca ttgaacatca gaagcaactc gaaaaactat tcaataaaaa    4260
tcagctcttg cctcgcatga ggaaggaatt cgaggactcc gaagaaattg actttaaggc    4320
attcgctgcc tatttggaaa ttgattataa gctgctcatt gacgcaatgg tgcagattgc    4380
cctacataaa cgtgctgaca tccaaactat gattggttct ctaatgagtc actcagatga    4440
tgctcagtac atcgctgact gtctgtataa gatggcagag aatgactgct tcaactatga    4500
ccctaccatc gacaagttcg tgttatcta tgagattagt gaagatgtac agatggaact     4560
ggaagcattc cagtacccat tacctatcgt aagtgctcct aagcctgtta agtgtaaccg    4620
tgatactggt tactacgaaa gcagaggtag catcatactt aagaagaatc atcatgagat    4680
ggatgtctgt cttgatcaca tcaaccgcat gaacaatcaa cgtctctgca ttaactggga    4740
cgttgctaac tacgtaaaag actcccgtcc taacatggat aaacccaaag agggtgaaac    4800
ccgtcaggac tatgagaagc gtgttaaagc cttgagaag tacagccgta cagctaagga    4860
agtaatggag ttagtgacca agaaggtaa taacttctca ctggctcaca aatatgacaa     4920
acgtgggcgt acatatgcct gtggctacca catcaactat cagggaacca gttacaacaa    4980
agctgtactg gagttcgctg ataaggagtt agtaaatgaa gactaacatt ggctcatatg    5040
agctatgggt taatgaagaa tgcgtttact ccggtacata tgtgaagtgc ttatactttg    5100
aaaagcttta caagcttcaa aaccctgaga gtaaaaccat tatttataaa ctatctgccg    5160
acgtagtaac tggctaatcc atccaataag caggctctcc atagtgggga gccaagaagc    5220
aaaaggaaca taaatgcaa ctgttaaccg ctaaacaata cctgaaagta gatatcgcca     5280
ataactatgg tctggataaa aagacatggg atgagcgtat tgcctggttc gatgagaacg    5340 aagctaaccct gcttaatctg gtagatgaag ctgaagattc tgcactgttc tatgctggtg    5400
taaatgcatg gaaagatatg aaagcaggta agcctattgg ttatgccgta gctctggatg    5460
ctacatcatc tggcttgcaa ttactggctt gtctgacggg tgaccgctct gctgctgaac    5520
tgtgtaacgt agttaattac atgggtgaga atgtaagcc attacgtcgt gatgcttata     5580
cagtcatcta tcacaagatg ttggacatcc ttggtgaagc atctcgtatt aaacgtagtg    5640
acactaagca ggcagttatg actgcgttct acggctcaga agccaagcct aaagaagtat    5700
tcggtgaagg tattcgtctc aagacttttg agaatgtaat ggaaactgtt gctagtggtc    5760
cttgggcatt gaacaagttc ttactgcaat gtggtaatcc agatgccaac cgttacatat    5820
```

```
ggatacttcc tgacaacttc cacgctgtca ttaaggtcat ggttccagaa gtacagactg    5880
ttaacttctt aggcaaaccg ttcgacatta ctcgtatggt tcagggtact gaagagaaga    5940
ctcgtatgct ctctgctaac atcacccact ctattgatgg gatggtggta cgtgagatgc    6000
tgcgtcgttg taacttcgac cgtgacttag tggaagctgt gcgagaactc tgcgatgaag    6060
gtccatcaga atatggggag attgcaggta atctggagaa ggtacaagag ctatggagcc    6120
attatgagaa gtctggcttc ttatctttat ccatcctgga ctatcttgac ccatgtacta    6180
ttgcttatgt agaccgtcag gtagtagcag atatgattga cactctgcct aagaaaccat    6240
tccctgtaat gactgtacat gactgcttcc gttgccatcc taactacggt aatgacctgc    6300
gtcgtcagta caatcagatc ctgtctgata ttgctaagag tgacctactg ggcttcatcc    6360
tgtctcaggt actggggcaa gagttctctg ctggtaagct ggatgacagc ctctggcagg    6420
acattcttga aacagactat gcgttgagtt aataaactag cctcattcct tcgggagtga    6480
ggcatatttt ttgcttggag gtaacaacta tgctaatccc ttttgaagta atctctcagt    6540
taatactgat agttttatct gtactggttc tgtctacaat agttcatgcc cacaaatcta    6600
agtttgctta ttactactat ggagcatact cactaggctg ctttgtaatg gcaggatgga    6660
tagcttttgc tatctactgt gtaaacaact aaccctccta acggagggtt tatttttta    6720 catgtcatgt atactaactc tgctatttac ttatgaggaa attgatatgc caactttgaa    6780
agtaggtttt aacaaaacca ctaatgttgc aactgtactg gatgccagtg gttctatccc    6840
aggtggttcc gtagaagtag gaacctttgt acacccagat gccacttacc ctgatagctt    6900
agttatcttc catggtgttc gtgacctgct gtataaacgc tctgctaaag atccttctaa    6960
agaaggcttc tggcctaaca acatcgtgga tatgcagtct atctctattg atatgaaagc    7020
tactccacga ctgactattg ctaccaaact gcctcgtgta gtctctacta tcgaaggtga    7080
agacatcaac tggcacgttg atgtagcagg tgggaaagca ccatttactt ataaatggca    7140
attcaaagct gatactgctg gagcagcatt cgctgatatt gattcaggtg agaacgaatc    7200
cgctgctact gcaacactga ctcttaatga cgtaacagct acttctgctg gtacttacaa    7260
agtgattgtt actgatgcta atggaaccac ggtagaggat gagtcactat tagctgtagg    7320
ctattacgaa gcaagttcac tggtagctac tcctgattcg ctggctctgt ctgttgctgc    7380
tgatacaact gctggtaaga ctgtaacaat tgttgctatg cctgttggtt catcttctgg    7440
tgctttatct atcaagactg ctccagattc tggtcgtgct acggctacca ttgctggtaa    7500
cgtactgaca gttaagccag tggctgctgg tgatactact tctgtagtag ttaccaatgg    7560
tacggtagat ataactatcc ctgttactgt tgcagaataa gggtattctt tgtttggggt    7620
tataaaccct gagataaaac cctcaagttt gacctcccta ttgaagggag gtctttttt    7680 gacttaagca tcctggagcc aggaaatgta caaagaaatt gcattcttct cattcttatt    7740
aggtggttta ataggtgcag gatttgtagc tatttctaat acctactttg gttctactcc    7800
aaattctgta acgcaaaccc tcaagcatga atgtgaattg aatattcctc gtaatcaaaa    7860
ctgtgtaatg cagttcgtac cggagaagaa atgaatatcc acaatctaca tttggttgag    7920
aaactgtatg aagaatacaa caacaaccga caacaattag ctagtttgaa gaagtcacca    7980
catatggtga agtatcatt caatggtacg gatttaggac cacaagcccg tacaagaata    8040
cttcctggac tactgtcctt ttatcaaagg agggttgctg ttttagagaa acgctttgaa    8100
catttaggtg tagatttatc accacttcca gatgaaggag aagagggatg aaagtaacaa    8160
atcgttctga gaacaatgag gtaactttcg gtgatgtgga gcctgctaat ggttttattt    8220
```

```
ataaccagac agtgtgttta aagattcact tacctgatgg taaacctgct gctgttgctg    8280
tagaaactgg taaatcattc tgtctatctg caagtacatt cgtaacacca ataaacctgg    8340
aaggatatta cctttgaaat taacacagtc ccaagcaatc ttccttcgta tggttcaagg    8400
tggctctgcc accagcaacc gtaataacaa aaccgcacag tctcttaaga agctgggctt    8460
agtacagttc aatgctggtc ttgggtggtc attaccccct atcggtgtac ttaaactcaa    8520
tgaattaaaa ggtaactaaa tgaaaacttt atttaaaggt attgcagtag ctgcactgat    8580
agctttggct ccaaatgcac aagctattga accagaaccc attttggaag gtgctcaggc    8640
ttatctggat gacactcgtg atgcgttcgg acaaggattc ttcatgggta gtatgatctc    8700
ttacatcgag agtactaata actgtgttcc tgaaggtatt aagtattcgg tcattctgcc    8760
taagattgcc aaagtagtta tttatgactc tgcaatcctc aagatgaaga atacatctca    8820
aattgttgtg tattcagtac acaaggcgta tccctgcact aaatcttaat tagcaattcc    8880
attagcttta ggagagtaag taaatggcaa gcatcgactc cttgaccgta tgtaattcac    8940
gtcaagcccg taactttatt atccgtgctc tgaaagcagg taacgtaccg ttcctgactt    9000
catcacctgg catgggtaaa tctgcaatca ttcgttctat tgcagaagaa tttggtatga    9060
aactgataga ccatcgtctg tctacttctg ccccggaaga cctttctggc ttaccattcc    9120
gtaatggtga ccgtgcagag tttatcccat tcgctgactt attccgatt gaggggatg    9180 aagtaccaga aggttataat ggctggctcc tgttccttga tgagttcaac tcagctaaga    9240
aagaagtagt agctgctgca tacaaactaa ttctcgaccg tatgactggt cagaaaaaac    9300
ttcatcctaa tgtgatgatt gtctgtgctg gtaacaaagc tactgaccgt gccattgtta    9360
atcctctggg tactgcaatg cagtctcgtg tggttcactt tgaaatggaa cttaacttcg    9420
acatctttgt tgaagatgta atgattcctc aacaatggga tgaacgtctg gttgcatttc    9480
tacatgctaa cccaggttat ctacatgact tcgacccagc tcataagaac aaaacgttct    9540
gttgccctcg tacctgggac tttgttaata aagacctcaa gaaccttcca gaaggtgctc    9600
tgcctgatga agattccctg tactacagtg gatttgttac acctggtaag gctgtagagt    9660
ttgttcaatt cactcaggta tataatcgta ttattacgat tgagaaagtg gtcaaagacc    9720
cattgggttg tccactaccg gaagataaca acctgtgttg ggctactgtt aaccatctag    9780
ctaacaaaac tactgaagag aacttcgctg atgttcttca gtacatcgaa cgctttaaaa    9840
cgttcaccca taagattctg tacttccgta cagtaggcag aacattacca gaacttcagg    9900
ctactcctga atggcgtaag gctgctgcta atatctctcg ttacattcac ggataaaaca    9960
atgaaccaat ttcctcagca cacacttagt gatgaacaac tcatgcgcga atatgaccgt    10020
attcaggcgc aggcgtttct cggacgcagt gctgccttct ttggttcatt actatgtagt    10080
cttaaattct catggaaacg tgaggattgt cccactgcat gtactgatgg gatagaactc    10140
catttcaacc cagacttctt tatctggatg tgtccagatg caaggggaaac agtattaatg    10200 catgaactat ggcatgtggc atatctacat gacatccgtc gtggaagccg tgacccggaa    10260
gtctggaacc aggcatgtga ccacttcatt aaccttcagt tagaggagga tggttacaag    10320
ttcactggta ttaatgaagg catttgcaaa gaccctcaat ataaaggatg ggtcgaagaa    10380
gacatctacg atgacctgat gaagaaccct cagaaaaggc agaagccgtc agggggtgct    10440
ggagcaggtc ttgctggcga catgaaatcc cccacttcgg gacagtccca gggtgctgtc    10500
gtcaacaacg tagtacgtgc aatgcagagc cagaagatgg ctggtggaac aatgcccggt    10560
```

-continued

```
aagggtgctg gtcgtatgga agaggttatt acccaattcc ttaaaccagt ggttccatgg    10620
caagaagtac tcatgaactt ctttaccgac attgatgaca ctcactatac gtgggccaga    10680
cctaaccgtc gttacactga catttatcta ccttccctgg aagatgatga aggacgtcta    10740
cgacacctag cctactttga ggatgtatct ggttctatta gtagtgctga ctctctgcgt    10800
tttaactcag aggttgccta cgttaagagt caattcaatc ctaagaagat gaccctaatc    10860
accttcgacg atgttatcca ggaagaaata gacatcactg aagaagatac tttcgaagag    10920
attaagatta ctggacgtgg tggtacaaac ctggaaccag tacgcgaatg gattattaag    10980
aataagccaa ccgctgcaat catattctct gatatgtatg ttcgtccaat ggaagaattg    11040
ccatttgata ttcctatcat ctggtgtgtt ctgaataatc ctaatgctac cgtaccttt    11100 ggggaggtag ttcatatccc taaggaatg aaataatggt tgttaatggt aattctctat    11160
atcgttcatc tcagttgctg gatgtcccag accgtaagat atccgagcat ggtgtaagct    11220
atggattagg tgaagctggt tatgatattc gtatcaaaca ggatattacc ttctatcgct    11280
tatttgggtt gattccaatg gtgaaggtcg ttgatagaaa taaagtatca cgccatttcg    11340
gcaagttcac attggcttca gcaattgaga agttcaacat gtccccttcc tgtgtagcta    11400
tcgttcacga taaatctaca tgggcaagac gtgcattatc tgtgttcaat accgtaatag    11460
agccaggatg gaaagggtat ctcaccctag aactggtcta tcatggtcgt aagaaattgc    11520
atatcccggc tggtgctggg atagctcaag tattatttca tctggttcag gaacctgcta    11580
attacaatgg caagtatatg aaccaggaaa accaaccagt agctgctaga tcctcaaaat    11640
aaaggactat ccagcttaat caaggaaaca acatgtcagt atttcaagta actcaagaaa    11700
gtacaggtat tcgcctaacc attaatgcga accaagtgat tgcagtacaa gaacttaccg    11760
caggtaactc tgctattact accgtaggag gtgatgtagt aattaccaaa gaaacctatc    11820
gttcagtacg taattacttg aaaaaagctc ttgctcctgc aagcaaagat gctgagtaag    11880
tagctgccta aatagcccag catagttggg ctatttgtga agaaactaac tcaaccccac    11940
ataggaacca tcatggaatc tttagcagca atccttgttc tgttatttgt attagctgta    12000
taccttatcc ctactattat tgcttttgca cgaggacacg cctctaagtg gggtattggt    12060
gtcctaaata ttgtattagg ctggtcttta gtcttctggg tagtagcact gatttgggca    12120
ctgtctaata aggtcagaa tcaagttaca aacgtaactg ttgttcaaac caatagtggc    12180
agtaaaacag agtaactaac ctaagcatca ttgcatagtg gtgcttgtgg aagttacttc    12240
cagctcattg cttatccatc tcctaaccca agcccaccta acccgtgggc tttttttatt    12300
acaggtactc ttatgtcaag cagacaaaat ggtaagtcta tcctgcaagg actggactta    12360
agtaagctgg aacaaactgc aatgcttact ttaggtaaaa ccatacatga ccaagtggaa    12420
atggatggga ttagttctga tgtctatgca aaaatgcagg ctcttattca gaaaggatgg    12480
cccagcagag tatttaatat acctacatac attcccccag aacccatct gaaatctaag    12540 gtagaccgaa tcatagataa gttctggctt aacccatgtg gagatgacat gcatctttac    12600
ctggctcaaa tacaaagaa tcctcgtact aaggatgtgt ttaaaagtaa gagcactacc    12660
catcactacc catggtatag aaggggtagt aaatactaat gcgtatccca ttcctaagaa    12720
aaagggaaca aaatcctgtt ctttataata aaggcataga ggatgagtat gaactcaacc    12780
gtaaagctcg ttcctacaca acaaaattat ttatggggac taaaacccct gatagattac    12840
tggactttgt ttttgaacaa gtcttttatca tatacagctt agctatgtct gctggttcac    12900
aagaagtaag tgataaggca agacatgctc tctgtatgct ccgtaaagag tatgaagccc    12960
```

```
tcatgtatga agacttgtac tcctttaaag aagaaaccgc tgtagcatgt tctgtggctc    13020
ttactgaagg tgtagcagta ttacaagaac taccccgtag tgagtttaag ctggtatacg    13080
ttcaggttaa gagaatcaca gagacaagaa gtggtatcac taactatcta aggtcattct    13140
aatgattaag gcatcagtaa ttgcagattc cgttcatcca gaaacaggaa cccgtatcac    13200
aacctttgaa ttggtttatc cccgattcat tcacagtgag tttatgactc accgtgtatt    13260
caaccgcaat gcttcaagta gccgtgctat tcctacctct aagttaatcg aacaggttcg    13320
caatgaacca gtgatgccaa gtcactgggg caagaaccag aaaggtatgc aagcagatga    13380
agaactcact cctatggaga ttgaggatgc taagtttatc tgggataacg ctgcatctgc    13440
tgctgctgtg tatgctgaac agctacgccg tgggcaagta cataaacaga ttgttaaccg    13500
tattctggaa cccttcacac atatccgtgt agtggtaacc tcaactagct gggctaattt    13560
ctatggactg cgtgaccaca aagatgcaca accggagatt cgtgaactgg ctcaagcaat    13620
gcgtaaggca cacgaagaaa gcacaccaag agcattaccg tatgggcaat ggcatttgcc    13680
atatattgct catattgacc gtgttggggc ttacaatttc tgcaaacgta atcgaattac    13740
acgcgatgaa ccaagtgatg aagaagtgca tggactactt ctcaaggtaa gtgctgcacg    13800
ctgtgctcgt gcttcctata caaactttga gggacgtccc tctactattg aggaagacct    13860
tggcttattt gctaagttag tggaaaacca acctattcat gcttccccaa cggaacatca    13920
agctacgcct atgaaccttg gtgagaagta tgtgaataac atgaacccag ttacctggga    13980
acaaggtgtt acatccatgg ataaagaagg gaatctgtac tcaggtaacc tgctccactt    14040
tatccaattc cgtaaattaa ttcctggtga gactattact gaatgaaaaa actagctcta    14100
tacgcaatgc taattagtac cctactaaca ctgacctacg catacaaagt tgcctttgtc    14160
gtagaaacag atatgcagtt cattcgagct agtattctgt tctttgtaag cgagattggt    14220
ttatggtgtg tttactactt tgctcgtgac tacgaagcaa ttcgtgagca agaagaagtg    14280
aaaaaacaaa tgatacgatt tgtagaacaa aatcgtaagt aaacctaaga cctcctccgg    14340
gaggtctttt tttggtttca attaactctt tcaggagggc atatgcctgc taaataccgt    14400
atcaaagaca cacccgtaat gtgtgagggt gagaagggcg acattgtata tgcctgtatc    14460
caggatgatt tcaatgctgc tcagatgcta acccaaatga caaatacact gcatgtgtca    14520
gtaacactgg accctaccgg tgactatcca tgcttcccta ttcctgccca taacctggag    14580
caaatccatg attaaccctg aagtaattca tagtaaaacc ggtaaggctg tcccactcag    14640
tgagattgca gtaactggtg atattgctgc ttgtccagct aacattgcct ctctatgcat    14700
atgcatcgct gcactagcag aggaacgtaa gttatggctg gaaccaagca aggaaatgat    14760
tcaggctggt ttagctgaag tacaaaacac gttagataac tgggaagaga acggcccact    14820
accatatgga acggtcaacg atataacaga tgacatggca tcagatatgg ctgtgtttgt    14880
attacaagca atggcaggta aacgcaatgg ctaatgtaaa tatcgcctca gagaaaacgt    14940
atagcattca gattaatggt ttaaccgagt atcaggtctt attcctaatg aatgcttttc    15000
aaaatagtcc tgtaggtcac catcctaatg atgaaccacg ggaagaagct gaacttcgta    15060
aagctatttt tgataagtgt aaacaagttc taatgtaagc aacatttaat ctggagagta    15120
aataaatgtt agttgcagat accaacgaaa tagctacctc agcgacactg ggtggcaaag    15180
aaacaattgc ctttggcatc tcagatgact cggcattctt ccatgtatta agtacttccc    15240
tgtataacaa tcctactctg gcagtagttc gtgagactat atgtaacagc tgggatgctc    15300
```

```
atattgaggc aggtaaaact gatacccta ttcgtatcac cattgataca gacaactta      15360
ttaccttccg tgattacggt agtggtattc cagatgaact cattggttcc atttatggtg      15420
tctatggtgc atctactaag aaagccaaca ttagtgttac tggtggcttt ggtctgggat      15480
gtaaatctcc attcgcttat acagatagct tacaggttac ttcatggaac caaggaaaga      15540
tgtctgtata taacgtagct aaggctgcga ttgagaatga tggtaagccg ggtattgtcc      15600
ctattgttac caatatacct actgaggaat ccggtctgga agttaaattc cagttaggca      15660
aacatgattt aaatacctt attcattaca tcaagtcaat cgtatttaac ggtgagatta      15720
aagctgagct tagtatccct aaactcgtta aaacggaaga aggtaatagt attcaacaag      15780
gtgactacac tttactgaat acgctgggca tgtcatttga acctggttca tatgatatgt      15840
ctgatagatg gtatcagggc tatatgggta gcagtaacat atacgttcgc tacggtaatg      15900
taatgtaccc aattgtatcc agcccagcta gtgaagaagc tgtaggtctt atcctcaact      15960
tcatgaatat tattggtgct gacaatttag tagttcaggc tgcaccagac accttagcta      16020
ttgctcctag tcgagaaaca ctgtctaacc agaagttaac cgacgatggt attactactc      16080
tatgcgtaga tttagtagac cgtatggaga aagagattaa ggctaagatt cctgaagcca      16140
ttaagcaggt tgaagaatat gcctctgaat cctctactcg cttttgggaa tatccatctt      16200
tcttgggtgc tgttacagat agaactgttc aacgctatat gtcttctagt ttatggacta      16260
aacaacgtaa gcatcacata aagcactggc gtaacttatc caataaggcg ttattagctc      16320
gtcctgaata tgcaggtctt aagaagctgt atggtaaggc tatgcatgct cttaaggata      16380
ctcgtgagga aagtacatac tccccattct cagaattagt atatcgccat ctgcatttac      16440
ctcgacttgc tgctttaaaa acctctggta ttaagtggtc tggttacata atgaatcaag      16500
gcaaccgtgt tgacttggta aaaggtaaac ttactgacta cttaggata tacaataact      16560
ctcaccaaag tattggcata tttactacca agaacgttgt agttactcga cgtttgtctg      16620
attgtgcaga ctctttctca tacttccctg aatacaatcg aggtgacctg agcgtacag      16680
cttttgttca tgtcgttggt cctaagaaag gtgcagcaga ggaagctgta gctaagttca      16740
ctgctatggg ttatcgggtg attgacctta ctcaatataa tgagtgggac aaaccaacta      16800
acttccgtag ggaacaggct aagatagctg ctgagaaacg ggctaagaca atagctgtca      16860
ataaaaccaa agcaggaggt aaaactaatg ctctgatttc attgaatgca gttcttggtg      16920
ctacccaggt acgtaataaa aatggggatt gggaacccag gccgtatatt cagaaagaat      16980
ttgctgaccc aagtcgtcat gagaaatatg gtttcgttga gatagaacag cctaagtact      17040
acgtactagc caatcaggtt ggttctggta gtcctgtaac tgctcgaatt ggaaccatgt      17100
ggaaatggta tgagttgcct gatgagatga aagcagagac tgttgtctgt cgtaatcaaa      17160
tcgaagctaa caaggccaaa cgacgaggtg ctatccacat tgatgatgtt cgctttagtg      17220
aattgatgtc tgttattacc agcaaaggct tcaagaaata tgttactgaa catcgcatcg      17280
gtattcttga atacgtagga ctggatgaca gggaatactg ggaaattcta gacatactgg      17340
gtctaacctt caaacccta cagaatctga ttttcaaacc agagtatgaa tgggcatatg      17400
acttttacg aaatcgacca cacgacaaca agaaaaact tgttgaaatg ggttgtatta      17460
agtcagttga tgacttagag ccatatgtaa aactggttaa tccccgtaac cataagtact      17520
ttaaagtact taatgattac aaagaattat tcagttatag ctggaataaa aatgacatcc      17580
tacagacgct ggacttaggt agtttggtca aacaccttaa gaagaatcca gaggatattc      17640
ctgggtttaa gtccctctac cgtaatcgtc taaataaact gaaaggtaac taatctgatg      17700
```

```
aaaatcgaac tgatttctat catcgcactg gcagttgaca gtcgtaacct tacattgtgg    17760
aagcccgatg gctccacgat tgtatatcct cagagagacc cacgggttgc tcgcattgta    17820
tctgaagctc aaactaaagg tctgggaact accaaagacc aaatagaagt aaacatcgca    17880
ccagaagtaa acctgcgtac tgaatatctg gaagcagaga agaacactaa cggattcgtc    17940
cgtttcttca aggtagctaa agctaaactc aaagagttct tccaggatgg tacaggtgtt    18000
caacctgacc gtattatttc tgatattaag ctgggtaatc ctactaagac actggtgtct    18060
aaagctatgg ataccttttct ggctgtacag gccaatgaac cagaagtaac tgtaacagat    18120
ggttgttatg acaaacgtga caatctgatg tgggttactg gctgggacaa agaccataac    18180
catcctgcac tggttcgttt tattaacgac gtaatgggtt gtgggtatga atatactaac    18240
accatgctca acaggaatg gcctgttgca gttcgtgcag tatctgatga tgaaatgggt    18300
gagtttgcta acaagccga acacatcaaa ggggttcatg ttgtattcac cagtcgtaaa    18360 catacccccac caccttacat tgaagtaact aaagttacga accaggataa gctggctgct    18420
gcctcggaga aactagctgc attgggtgct attagtactg atgacgctaa cttccacacc    18480
gatgtgaagg aagatgaagt ggttgttgct gttaccaaca atggggttat ccccggagtt    18540
gagaacctgc aacgtcactt acgtcagtct gccaagctga aagactacaa gggctttact    18600
aagttccttg aacgtctggc tccggttatt aaagaccgtc tgcactcagt agaagacctg    18660
atgaagttca tggaaactgc tgaactgcct attgccgatg atggttcaat cctgttcctc    18720
aaacgcctta agtctagtgg tatagaaaac ggtaaacgtg tattcgttga ctgtcactcg    18780
ggtaacattc gtcaatgggt aggctgtaaa gtgcaggtac gcgaagacct ggtagaccct    18840
gaccgtcgtc aggattgctc taacggtctg cacgtagcat ccatgagcta tctacgtggc    18900
ttcggtggta atgtgaccat ccttggtaaa gtagcaccgg aagatgtatt tgctgttcct    18960
cagtacagca ccaataaaat gcgtgtatct gcatatcata ttattgctga actaccggaa    19020
gaggaacgta ataatgttaa taatggtatc tacctgtcta agacagaagt aggtaagaaa    19080
ttgcttaatg atgccatcgt tgggaaccat agctcaccta ccacacttat tatggttggg    19140
ggtcattatg gtactaacct caaatacact aatctcacat ctggttctgt agaacaattc    19200
cgtacagttg ctagcaaaga agcactgaac atggaagagt cactgaatga agctgtagct    19260
gctgaaccag tgaaggctac tgaccttaaa cctgttatta agaaggctcc tactgtgaaa    19320
gaacaaatcc aggaactggt caaagagttc cttactgcaa caaccccaga agataagtta    19380
gctgctgctg accttctggt agaactgcgt ggtaaagctc gtaagccttg ggctgcattc    19440
gatgtgggta atgatgtagt agctaagatt gctgatgtac gtgctaccta tacagctaag    19500
cctattggta aacctaaagc tgttaagcag gataagacag ttaaacctac taaatctaag    19560
cctgctatta atagtactaa tgccaacatc atcagaggtt atctagcaga tagtggtatg    19620
tctgattatc agaaagccca ctccattcat gacctgaaac gtgcagctaa gaagtcttat    19680
gctgctatgg gtcttactga agaagagtgc aaagccattg ataagctgaa gcaccacctt    19740
aagtaatagc ctgttcaaat agcctcactt ataataaagt gaggctatct ttgaagagga    19800
aataagctat gtctaaagta ttcagaagta atcgcaaagc aactgatgaa gacatcattc    19860
gtatgaatgc tgttggtctg tccctcgcaa ctatcgctaa gacgttgggg gttcacccaa    19920
ccacagtcac tttgcgattg cgttctctaa acattgaacc agccgacaca cgtcggacgt    19980
tcatggaaaa cgtattacga cctttaccaa cccatgtggc tgattggctg tcagaacaag    20040
```

```
ttggtcctgc ttatgagatt cgctcatatg taagagactt gattctggag gcatataata    20100
atcgccacct taaccaagag agtgagcatg acaagttcat ccgtttgtac gctggcaaat    20160
acggaagcct ggttccggaa agcagtacca aatccgacaa gtaagaacat tagtacccag    20220
atgggttgcc atttggaaga agtagaagaa atgcttcaga ccatttatcc aaatggtagt    20280
tacgatgcag aattactgca acgtgcacag gatgccatta caaatctggc aaatcatatg    20340
aagcgtaaag acaatgccta tcgcattgat gttagtaccg acctgctgga ctcactggca    20400
gaccagattg ttacagcaac tggcgtcggt actttccttg ggatgaatgt ccctggagca    20460
ttggctgaag tcaatcgctc aaactattct aagtttgaag atggagaacc tgtcttcaat    20520
gagaacatga aagttatgaa agggaaagac tacactcccc cggatttaac cccttacatc    20580
taaccctcta cggagggttt tttactggag atttttaatgt tttccaaacc taccaaagcc    20640
ccactgaaca aggggcaaga agcggttgcg aaggagttct tcgacttcct gctcgaccct    20700
aatgctaccg aattcaatat tagtggccca gggggaactg gcaagacatt cctgatgtcg    20760
cacctcattg atgacactat gcctgcatat atggaaactt gctcccttat gggaaccaag    20820
cccctatata cgaagttgt tatgactgcg accacgaaca aggctgctga agttctggct    20880
caagctactg ggcgtccaac atctacctat cattccttcc agggattgat tgttaagaat    20940
gactttaaga ctggtgaggc taatgtcgta ccgtccaaat cattcaatat taagaagaac    21000
aaaatcatct tcgtagacga agcatccatg attgaccgtc agttacttaa atatgctcgt    21060
gaaggtactc accagtgcaa actggtattt gtaggcgatg cttctcagct tctgcctgtt    21120 aaaagagaata agtctccagt gtatgcaggt aatatcccaa cacactatct gactgaacag    21180
atgcgtaccg atgcaccgga acttaaagca ttgcaccagc aattgcgtga tacggtagaa    21240
ggtaagacag gcttcctgcc tattaaatgt attccaggca tcattgattg ggtacagggg    21300
gaagagatgg agaaactggt tctcagtcac ttcactcaac ctactaatag ccgtattgtt    21360
gcttacacaa atgaccaggt tattaattac aataactaca ttcgtgaagc taatggctac    21420
gtgggtgagt actccattgg tgaacagcta gtctctaact ctgctattcg cttaggtgtg    21480
gataatcgtc tgtctatcga gcaagacgta aaaactcattg accaggatag cagtactcgc    21540
atgattccag ttacagatga cctggaactg gaagttcgtg atagtactct ggaccttggt    21600
tatggtggta ttgtaagtga agtcccagta cctaccgacc cagaatactt caaccgtttg    21660
gttaagtggc taggtaaaga gaagaactgg gaaccctact tccgtcttaa agaaaccatt    21720
ccagacctac gtgctactca tgcatgtact gtccataaat cacaaggctc tacttacgac    21780
acaatcttca ttgatgcaga tgacctctca gctgtcgcc aacctgatat ggttgcccgt    21840 ctgcttacg tcgctgtgtc tcgtgcccgt aagcgagtag tgttttatgg caatcttgtc    21900
agtaagtatg gtggtctaac tttctaaggg aggatatatg cctcagattg gttcagcgac    21960
tattggtcag gttgccaata gcagtgagat agtcaaacac ctgttcttag cagaactggt    22020
tcgtcttgat agtgtgttaa acggtatcat tgataagaac gaccgtatca atggtattga    22080
tatatcggct ggatttcttt atcaaggga gttctatcag cgttctaatg ctgccagacc    22140
tccaacctac ggtgaacgat taacacttaa tccagaactt tggcctgcaa tggacaagta    22200
tctgaaagcc tccagtcgcc tgattatgga agtacacctt gtgaaccaga ctgtatatcg    22260
cctggttcgt ggttgtatgt cctatcagga tgtacgtgat gctttacctg aatgcctggt    22320
agcccaggac cagactggta agtacaagga actgccacgt actcgtgaag cagcctggac    22380
acttgctggt gatcctatgg caataaaaca gtatgagaag attcttccct ctattgagta    22440
```

```
ctatgcagct tcccatctga ttttctaagg taaggctatg cgttacatca cctctcagga   22500
tacgggtaag tatcctattg ctatcctcgg tcatcaaatc cgaagggagg agatgattaa   22560
aacctacctg ctgcctaatg acctaagcat ggaagatttc atcttcatcg aacttcattc   22620
tgcccccggc aagaagaaga ctcctgcaag ggagattaag gagttcatac agcaggagtt   22680
gcaacaagta ctggacgatg cagagactca atacattatc tgtaccgatt ctgactactt   22740
caaaatactg actaaagaag caaaagcaga ggctaacctc ggctacgttt gtgattcagt   22800
atggggtaag cagaaggtta tctatgcacc tagctacaga caggtctttt atgaccctcc   22860
tgtagtgaaa tctaagattg ctcagggtat ggatgcatta cttaaccaca tacgtgggca   22920
gtatgcagaa ccaggtcagg gaatcattga gtttgaggct tatccagata ccccagagaa   22980
gattaaagcc tggctagacc agttgcttga gatgaataag ccattggcta tagacatcga   23040
ggcattcggt ttaaagcact ataacgcagg tataggaaca attacgttct gttggagtaa   23100
gacacaaggc atagccttta atgtggacta cgagccgatt cctggagcta ctgaagcacc   23160
atacgggcgt atcaacagaa atgatgttgt tcgaaatctt cttcgtgagt tcttcattaa   23220
gtacactcaa cggcagatgt atcacaacat tagctacgac gtgtatgtgc ttatctatca   23280
gttattcatg gataacctga ttgatacaga aggcttactg catggtatgg aaatcatgct   23340
acgcaactgg gactgtacta agttaatcac ctacctggct actaacagtt gtgctggtaa   23400
tcaccttagt ctaaaagacc aggctcagga gtatgctggt aactatgctc aggatgacat   23460
taaagacatt cgtcttattc ctaatgagca actcttacgt tacaacctca ttgatggttt   23520
atgtacctgg tacacctatg agaaacactg ggatactctc attgctgatg accaactaga   23580
tgtttacaac aacatcttta agccagcctg tgaagatatt atccagatgc agttaactgg   23640
tatgcccatg aatatggata ccgttaacca agtagctaag gagatggaaa ctgacaggaa   23700
ccaggctctg aaaactattc gtgagtctaa gctcatgaag aactttaccc tgatgcttcg   23760
tcaggaatgg gtagatgata agaatgctaa gctcaagaag aagcaggtaa cacttgctga   23820
ctgtgatatc gagtttaatc ctaactccgg tccacaacta cagaagctat tatttgacta   23880
tattggctta ccggttcttg gtcttactaa gagcaagcaa cctgctactg acggtgacac   23940
tattaaagca ctgcgtacac acacgcagag cgaagatgtt aaggaactgc tcaatgcact   24000
tatcgactat aagctcgtgg ataagattat cacttcattc atcccggctt tccgtaatgc   24060
acaaccggga ccagatggat ggcactacct attcggcaac ctcaatctgg ggggaacggt   24120
ttctggtaga ttatctgcct ctgagccaaa cctgcaaacc attccgtctg gctccaaata   24180
cgccaagaag attaagaaat gcttcgaagc accccaggt tggatctttt gtggactgga   24240 cttttgcaagc cttgaggacc gtatctcagc tttaactact aaagacccta ataaattgcg   24300
tgtgtatact gacgggttcg atgggcactc cctcagagct aaattttatt tcggcgagca   24360
aatgccggat atagatgatt ctgtggaaag catcaactct attcagaaaa aatataaagc   24420
cttacgtagt gaatcgaaag ctcccacttt cttattgact tacggtggga cttatatggg   24480
cttgatgaaa aactgcggtt tcccggaagg gaaggctaag ttaatcgaat ccagatacca   24540
tgaaatgtat acggttagtg atgcctgggt tcaagctaag ctagacgatg ctgccaaaac   24600
tggttatgtt actgccgcat tcggtttgag agtgcgtact cctttactgg ctcaagtatt   24660
acgtgggaca tgtaagactc cgtatgaagc agaagcagaa ggcagaactg ctggtaatgc   24720
tttagggcaa agctggtgtc tactaaataa ccgtgctggt tcagagttta tgcgtaaagt   24780
```

```
cagagccagt gagttcaggt tagatattcg tcctagtatt catattcatg atgctcagta   24840
cttcatgatt cgtgacaaca tggatacttt gcaattcacg aacaagcact tggttgaagc   24900
cgttaactgg caagaccatc ctgatattgc tcacccagaa gttggtttgg gtggggaact   24960
atccttgttt tacccaacgt gggctaacga gattgaaatt ccaaatcacg ctaccccaga   25020
agaagttcat caaataattc aaaaggcatt cgcatgacca aaagtactaa agaaactgtt   25080
gtcagaaaat atcattggat ggtagcagca caggtagtat tccaacttcc taaagtggat   25140
gatggttccc tgcttaccat gaacacaatg ttgctcacag atgaacctta cgtgacctat   25200
aaagatttgg ctcgtgccaa tcactctctg aaaatcagtc tggaccagcg tttcgacact   25260
tcagttgact tgaaagacat cgtttatctg tctcttagca acctgggtct gatgtctgaa   25320
ccagagttcc aggcaaacat gattcccaag gagaaataat ggctaagctc tccggtggat   25380
tgaataactg gtatgtagta ccagttaagc accctcaacg gaaagagcaa gagccatacc   25440
aagcagagtg tgaggatatt atccaagcac tgggcatgac cttcgatgaa ggttgtgcct   25500
ttaaagctct atggcgaaat gctgctgccc gtatgggtaa tggtaaacct ggaaacactg   25560
ctgtttacga tgcagagaag ctggttcatt atgctaatcg tattcttgct aaggagaagt   25620
tagctagtga gttatttccg gatcctgcta cgaatgtaaa taccgttggt agttattggc   25680
accatacaaa caatggtaaa cctcacttca ctaaagaatt ttcattcatt gagattgttt   25740
ataaagatga acgagatgaa atttactcgt ataacttcaa tcagctaagt gaaattaagt   25800
ggaactgggt tcacagatac aggattactt actaatgaag ataaccaaca accatgatgt   25860
atcactggcc ctggctgtat ggctattgca tgacgagtaa ctaattatga acagaggat   25920
tgcccatgac aggcttttac agcttgttag ttatgaccct atttccggga tttttactcg   25980
taggaatacc ggaaaggtat ctggttacct aatgaagagt ggttacgttc aactccgtgt   26040
ggatagtgtg ttgtactatg ggcatatcct tgcatggttc tatgtgcacg gtgtatggcc   26100
tacggataga attgaccata aggacaatat tcgccatcac aactggatag ataacctcag   26160
agaagcgacc cacaagcaga ataaccagag tgctgtttta tctaaaacaa acacatctgg   26220
atttaagggg gtatccttt caaagaattt aggtaaatac agagcaacta tttgggttaa   26280
cagtaaacca attacattag gttttacaga tgacccaaga gaagctgctg ttctctatga   26340
tgaagctgct ataactcatt atggtgagtt tgctaaaact aataagcaat gggactgtt   26400
atgaaactta ccaacaaaca cgacgttagt cttgcactag ctgtatggct tgtaacggat   26460
gattatgatt atgtagacaa tcctaagtat ctgtctgtta ctaccttgct taagcccatt   26520
aagcaaatag tcatgaagca tcgtgtagat cttagtgacc agtcaattga tgttatggat   26580
ttcgtctcca catcaatggg tactggttta catgattcta tcgagaaggc ctggaagctg   26640
ggtcataaga ctgcattgaa aaagttgggt tatcctcaac gagtaattga tgcagtagtc   26700
attaacccaa ccaaagcaga ctttgatgct aaccctgacc ttatcccaat ctacattgaa   26760
cagcgtggaa ccaggatagt taagggttgg actatcggtg gtaagttcga catcgtaaca   26820
gaaggtctgt tgcaggactt taagtctacc tcaacctatt cctgggttgc tggttcccgt   26880
gatgatgaac ataagatgca aggcagcttg tatcgttgga ttcacaacga catcattacc   26940
gaagatgtaa tccgtattaa ctacatcttc actgacttca tgaaacacat ggctaatagc   27000
aatccgaact atcctgctaa tcgtattatg cataaggata ttccgttgct atctgtcgag   27060
aaaactgaac gttgggtaga agagaagatt cacctcattg aaaagtactg gaatgcacct   27120
gaagaggaaa ttcctgaatg tactgatgag gagttgtggc gaacagagcc acagttcaaa   27180
```

```
tacttctctg atgcttctaa ggtagatgta cctggagcca gaagtaccaa aaaatttgac    27240
gatatggcat ctgctcgtat cttcatggct gaaaaaggtg gcaagggtgc tatcaaggtc    27300
gtggaggggc aggttaagcg ttgtctatac tgccctgtcg cgtccatttg caaacaaaga    27360
gagagatatt ttccatcatg agtattgacc tgaccggagt cactcaccac cctgcaattg    27420
aagaaattgt agacgtgctg tgtaacaaga cacaaaacaa cgacagagga ttcttccgtg    27480
tcgaagtagc ctacttcctg gctaaaatgg catcctgcat gggtgcaacc attgtcacta    27540
aagaccgtgg tgacttacca gtcaacattt acgctatggc attagcaacg tctggcttcg    27600
gtaaaggtca ctcggtaaat attattgaag acggcttcat gactggcttc cgtaaacgtt    27660
ttatggaaga caccatgccc gtcattgcaa atgaccgttt atggaagatt gctaacgaac    27720
gtgctgctcg acaaggtaca gaccagaatg atgagtttga taaagtcgaa gcagagtata    27780
aacgtgctgg agcatatccg tttacgtttg actctggtac tccaccagca gttaaacagc    27840
tacgacataa gctgttaatg gctgggtgtg gttcaatcaa cctacagatt gatgaaattg    27900
gttcaaacct gttggctaac acggatgtat taactctgtt cctggaatta tatgaccagg    27960
gtaaggttaa acagaagtta accaagaaca ctgctgaaag tgttcgtggt gaagaactgg    28020
atggtaagac tccagctaac ctgttgctgt ttggcacgcc aagtaagcta ctagatggtg    28080
gtcagaccga agaccagttc tatgactttc tggatacagg gtatgcacgt cgttgcttat    28140
ttgccattgg gcatttagat aaacgagcac atgcaacaat gtccccagaa gaaatctacc    28200
gtaacctgat taagcaggat aacgtacagt ctctgggtaa gtgggctaat cacttccaca    28260
gtctggctga tccaaacttg ttcggcttta agatggttgt agaagatgct gtgggtattg    28320
ctctgattac ttacaagatc gattgtgaga acaagcaga agctatggct gaccacgaag    28380
aaattcgtaa ggctgaaatc tcccaccgtt actttaaagc tcttaagctg gctggagcac    28440
tggcatttgt tgaccaaagt tcattcattg aaatgtctca tcttaaacaa gcaatcttgc    28500
ttgtagaaga atccggggca gcattccagg gtattctcaa tcgtgagaaa gcctatgtga    28560
agctggctaa gtatatcgct tctgtaggta aagaagtgac tcatgctgac ttactggagt    28620
cgttgccgtt ctataagagt ggcaatgcag ctcgtaatga gatgatgact cttgctacag    28680
catggggata caaacagcac atcatcatta agaaaacttt taatgaaggt attgagttct    28740
tccgtggaga gactctgaaa gagactgaca tcaatgagat gatagtggcc tatagtgata    28800
gctttgctta tgactacatt ggtgaacgtg taccgttcga ccagttgcat gtattaaccc    28860
aagctcccgg tatgcactgg gtaaaccatc acatgaagaa cgggcatcgt tccgaagaga    28920
acgttattcc aggatttaac atgattgtta ttgactgtga tggtggagta ccactgcata    28980
cgtgccatga actgatgaag gaatataagt tcatgaccta taccactaaa cggcattctg    29040
atgaagagaa ccgcttccga ctgattattc caatgaacta tgagttacac ctcgacactg    29100
aggaatacaa agagtttatg aataacgtta tgtcttggct accgttcgaa acggatgaat    29160
ctgctaacca gcgagccaag aaatggatgt cctgtgagac tggttcctat cattacaatc    29220
ttgaagcaaa tctgttggac gtgcgtgact ttattcctcg tactagtaag aacgagcagt    29280
tccagaacca gatgaaggaa gtacagtcgt tggataatct ggagcgttgg ttcgctagtc    29340
gtattgctac cggtaatcgt aataatcaaa tgattaagta cgcactggca ttggttgaca    29400
gtggttggga ttttgcccaa gtacagcaag ccgtccactc attcaataag aaactggcta    29460
atccattacc agatgatgaa ttgaatgcaa ccgtaatggt caccgtggct aaacgcttcg    29520
```

```
ctggcaaata agcaaacagg agtctttctt tggtttgaag gactcctaaa ttaaatgagg    29580
aaaaataatg tccgaagtaa ttcccaatga tatgaacact cagctaatcc tgattgcagg    29640
attctcagcg agtggtaaat cagcatcact gcgtaacatc aggaaccagg aacgctggct    29700
ctatctgaac actgaggcag gtaaacgtct acctttccgt aacaagttca atacctacaa    29760
catcgaagac ccataccaaa tctgggaagc atttgatgtt gcatctcctg gtggagaaat    29820
ggcagatgat gttgatggta tcatcattga ctcagcaact tttatgatgg atatgctgga    29880
atcccagtat gttctgcctt ctgcaaacac gcaaaaggca tgggggatt ttgcacagtt     29940 ctttaagata ctgctgcaac aaaaagtcgt taagtttggt aagccagtaa tcattactgc    30000
tcatgctaaa gacgaactgg atgaagctgc tggtgtgatg aaaacgttca tcccagtgaa    30060
aggctctctg aagaataacg ggcttgaagc ctacttctct acagtggttt acgcagaacg    30120
tgtagacatt aaagaactgg agaagtatgg aaacaagatg cttgaaatta cggaggaaga    30180
acgtgattta ggctataaac atgtattcca gacccgtcca accagaagt ctgttggtaa     30240 acgacttcgt tctcctatgg gtatgttcga taagtccgag acttacattg ataacgatgc    30300
ccagaaactc ttagaccacc tggctgaata ctacgcttaa gcgtttgtct ggttgttaat    30360
cacttattag gaaaatcata tgtcattgtt cagtaatctg aaagaaaaaa ccaaaaacgt    30420
tgaagctgct aaagactctc tgggtggtgg tggcttcggt gcaaagaaa ccgatatcta     30480 cactggtact gtaaaagtag cttacgtagg caaagctgat tctggtgcag actggatgca    30540
gttaattatt gaagacctga aaaactctga tggcgtgcct gctggcgagt tccgtgctca    30600
ggtgtacttc acttctggta atgctaaagg caacaagccg acttacgaga aaatggtaa     30660 agagtacttc ctgcctggct acactgtcat taacgacatg atgctgatgg ctactggtac    30720
tgaactgcct gaagcagact tcgaagagaa gattgttaaa gtctacgact acgacgctaa    30780
agcagaagtt aataaatctg tcatggttcc agttgacctg gtaggccaga ctgttacctt    30840
cgctctggaa aaagttctgg aaaacaagca ggttaaaggc gacaacggtt atgtagactc    30900
tgacgaaact cgtgaagtaa acgagattca gaaagtgttt cacccggaac tgctggtcac    30960
agtcgtcgag gctcaggaag cagagaaggc tgaaaaagaa ctaaccccag aactggctgt    31020
attctatgca gcatggctgg aaaagaacaa aggcaaaact cgtgacaaga ctaagagttc    31080
tgctggtggt aatggtaaag gtggcttgcc tcctaaacca ggtgcaggtg ctggcacggg    31140
tactgctcct gctggtggta aatcactgtt tggtaaacgt aatgaaaat cccaattgtc     31200 ggtgcagaca ttagtctccg caattggggt ttagctcgtg gatgctgga cattgagtcc     31260 ggcgtcttcg agcaggtcga acttaaactg gttcaaactg aagttgacca caacaaacaa    31320
gttcgaacca actccaaaga tatacaagcc gctcacgatt tgtttcttgg ttgtgaggaa    31380
tggttacggt ctgctaaagc agtattcgta gaagtaccag taggctctca gtctgctaac    31440
ggtatgaaat cctatggcgt atgcgtagga ttaataggtg catttcgtgc attgggttgt    31500
ccaatctttg aagtatcccc aattgaaaac aaacttgcac tggtcggtga taaaactgca    31560
tctaaggaca cgatgattcg tgctgctcat gccatctatc ctgaagccaa ctggctcaca    31620
gataagaagg gcaaacttct gaataagaat gagcacttag ctgatgcaat cggtgcaatc    31680
catgctggtg taaatctccc agctttccaa aacctcctta atttaataaa ggcgtaacat    31740
gcaaatcatt ttgaaccagt ccgaagtaga agctgctgta caggcttatg tcgatgatca    31800
aatcaatctt gctggtgaca tcaatattgt catcaatgca gacggtacag cttccgttgg    31860
tatcaacgaa gaggttcatg aagatactcc acccgtggga gtagagaaga aaactcgtcg    31920
```

```
ttctcgtaag aacccacagg aagctaaaca tcgtccggta gaaccagagc cggaagaagt    31980
agttgaagag gtaaaggtag aagaaaccca gacctctact ggtggtcaga acgagagttc    32040
tacgccggaa cctgaagaag aagcagtatc tgaaccagaa gcacaagaag aagttgtgca    32100
ggaagaggct aaggctgaag aaccagcaga gaaacctgct actaagcctt cactgttcgc    32160
tggccttaaa cgtagttaat ctggtaggtg gctcagaagc tgctgctagg tgtggtagtg    32220
tttatagtcc taatgctact actggtcagg attatagacg tgtcggctcc atacatagct    32280
tttatcatca ctgtcattat cctgtggaaa tgcagtggta acacggtgg tgacaagccg     32340 ccagagtaac aacaacaacc gaaccagtgg actttaatac tctccgaagt ccattggttc    32400
aactgagact aatatgaaca aatttactat tcactggctc aacggaaagg ttagttcttt    32460
catgggtgga gaacccgttg aaggaaagaa agcatttcac attgaatcag aaggctgcaa    32520
aatcttagta ccatatgctt ggtatagaga gggtgaagta gaagcattaa aaaagagtag    32580
ttaatatcgt gaagggttct gttagaatcc tttgagatag gaactcctat cataaccttt    32640
cttaacttaa tctttgccgt atggcactga cgctaggggt ggcccccat ccgtcaggta     32700 aactatttta agaatgggtt atcacagaaa atgtaaagca acattcgggt taatcaatgg    32760
cctctcccta taggggccat ttctgaatga taggctatat cccaaaggtt agtatctttg    32820
ggataaggct tcagatccct tatcaaacta accgctcaat gttgagcatt ttaatcacat    32880
aagcccctat atgggctggg ttaaatgtcg gatagcatag ctacctacag catcgaattg    32940
ttaggtctta catgcaatat agggtataaa gggaggactc gtcccctccc tcctattata    33000
atggtcgagg tagcacgtag gcatgtgcag agggtcgcta cttctctcgc tggttcgaat    33060
ccagcccccg acctactgac atcctatcaa tgagtacatt aagctaacgt gcggaggttt    33120
acactgtagc cggtgtaggt ggagaagacg gcagggtagc tacctgtgct tagtgtactc    33180
tttgatagtt ttcgtaagcg attatgcggt tttttagaaa cgaaccaata acataaatgc    33240
aaacgatgat gttgttctga tggcagccta ataagccaag cgtcagtcgg gagtgagtcg    33300
tcctgattat caaacgacca tggagtgtcc tcgtccgtgt attagaaacg gggagttaat    33360
caatggtgtg tgatagctca aataggtaga gcgtgaggc acagtgctga atggtttgtg     33420
ggttcgattc ccacccatgc ctacagtcca gacgatatct gagtgactat aaaaacagat    33480
ggagccaggt ggaatccctg gcaattaatt ccggtgtagg tactagtgtc gtgcacggca    33540
taagtgttct ggttcgagtc cagacgccgg aaccaattat cagttgcacg agatggcttg    33600
atatgttcaa gtttggacta agtgtgacac cgctagattg gagagctgct gcggtaagct    33660
atagactcca accgggggtt cgaatccctc actggtaacc aattcaaagt agcattgcat    33720
agaacgcgaa aaggtacagc gacgttgcaa accaacggta ttgtaaggtt cgagtcctta    33780
cctatgagca gtgacgactg caacagtgct actctgaatt gtaagaatta tggtgggtct    33840
ggtgaagtag atagggttcg attccctccg gtagagtaat ctactagcgt gcttggagca    33900
cgaataagac ttaatactgg tggttcgatt ccatccccca ctgcctattt gaggtgtaac    33960
agttaaatcc agttgccgga agtgctattc tagatacgct gccaatgtgt gaacggtaag    34020
gctgtacagg actcggactc ccgcctcaaa ccaaagtcgc caggtactta tggcaaacgg    34080
gtagtaacga actagtcatt cgtcaaacgc ccaccctatt atgagtcagc aagaacgcct    34140
tcacttaaac ttaaacaata taagcttaac gcaataatta tgtaggggta tgtaaggatt    34200
gcgaagaagg agccagttaa agtctggcat gactcactca tttatgccca cttagcttag    34260
```

```
acgggaaag caaccgacta ataatcggaa ggtcactggt tcaaatccag tagtgggtac    34320
ttattaatag agaacatagt cctgattgca ttgcactcta aagacaatgc cggtgagaca    34380
gtccggcact ctaattattg aaaacatacc taacggtgtg agtatgagca gactataatg    34440
ctcaattaca gttaactatt atcggactat caatcctgtt tgctggtaca agcaccggtg    34500
gtaatagtta actggcctag cctcattagc tgcgttaaag ctactaagtc cctcttcgga    34560
gggacttttt tatttgagta ttgatgaacg caatcatgct taagtacaaa ttcaaaccac    34620
tctatgaggc taataatggc aacagtaagt aaaaaagcaa tcgaagctaa gattaagagc    34680
gtttactatt ttaatggtgc tgatgcagtg aaatctgcat tcgttgatcc ttctgcactc    34740
ccggcagatg atttggctaa cctgggtctg gtaacctatt gtgttatcat tctggaaaac    34800
aattttaaag ttgaaggtgt atctgcttgc gtagacccaa ctatctatga tgagcagtta    34860
ggtcgccagt atgcatatga aaatgcattc aataagattt gggaattaga gggctaccta    34920
ctacgtcagg cactgcatga gaaggaagag actgctaaag ctttggcttc ctttgcagaa    34980
aacaatacct gtgatggtgg tggttgtaca atttgattca aaggtgtatg gtagtttta    35040 ccgaaaggta ctgaactacc cgacaaagta gtaaggctca tgaagccaaa acaaaacaag    35100
ccctcctagt gagggctttc tcatttgagg tagttatgtc agaagaaatt aaagtccatt    35160
tcaccaacta cattggaacc aagtgtgtaa atggttttcc gatgagcaaa gaaacatact    35220
gcaaacttcg tggttgggat gtaccagcag atgaagaccc gctagaagaa ggctacttag    35280
tcgagtatcc agactctaag tccaaccatc cccaattccg tggctatatt agctggtcac    35340
ctaaagctgc attcgaagct gcataccgtg acgtagaaaa aggttgtacc tttggtcatg    35400
cagtagagct tctcaaatca ggctttagaa tgacccgtaa aggttggaac ggaaaaggaa    35460
tgtatatcac cttagtatct ggtgaaaatt gggccatgga taaacatgaa ataccgttt    35520 gtgagaaacg ggattggctg gtattaaaa ccgttgataa ccagtttatg ccatgggttc    35580
catctcaatc agatgtatta gcagaagatt gggtgttagc tcagtaaaaa taaaagcccc    35640
tcattagagg ggcttttca tttagttagt aaggttgagc caagggttca ggttgtgggc    35700
acgtaagcct tgaccgaaac caaaggagta accaagattg ccttgtgcag caatactaaa    35760
gatgttgtcc tgaataggaa gaccaacgtt accaaacatg gtaggggttg gagccaacat    35820
agccatagca gcatgtactg ggttattacg aatcatggac actgcaactt ttgcagaacg    35880
aatcttaaag ttgtagaacc acatcaaacc aacactttcc atatacccac ggaatcgacc    35940
aggcagacgg tcatagttaa tgaactcttc cgttacacgc cccagtgctt cttcacgagt    36000 cttacccttta cgctgagtca gttcatcata gatgattgct ttagcaataa agtcagagta    36060
ctcaaccgtc ttctgaatac cctggaagag agcagtatcc ttagtgataa gtgcatagcg    36120
acctgcgtta cgaacagact taggcagctt atcagccagc ttttccatgt attcgtggag    36180
tttaccttca gtaatcagga tgtcatcacg accaatacca gcatctgcaa ttgaagagaa    36240
ctcaccagct tccaacagag gccagatact caaacgttta tggctatcag agatggactg    36300
aatctcagcc ttgagtttac gaatctggtt cgggttagta gctgcacgta attctgcttc    36360
tgcatctacc tgacgcagac gagatttcag gtactggtta atctcagcag tcttctgtgg    36420
aatgctctta gcaatgttct taaccggtac accacgagca accatctgat aaaggttagc    36480
caggaagtta acagcaggta cgactactga cttaaccaca atcagagtct tagcttcttt    36540
aactaagttc tgaaccaggt tctcaccacc cattacatac ttataggcac ggttgccaaa    36600
gacacccagc atagctttct tgaaggtatc cagtgtttct ggtgaccaac gggaattacc    36660
```

```
agaccaggca tcacctacag aagctgcacg ataacccaga gcatcgttga gcatgtcacg    36720
acgtacccat aattcacccg gaccaaacaa actttctgct ttctgacggg tttcactgtt    36780
catcagctta agtgcatcgg cagttactgg gtccagttta gaaccaagaa ggttaacgta    36840
ctgggactta ttagaagcag acatcttaat gtcgttctca tacatgctat gcaggttttc    36900
aatcagcata tcgttgaatc gctgagcctt agcttcttcc acctgacgac cacgccatac    36960
accgattgca cgagcaagat ggttctcacc ttcaatgtgc ttcagcatgt tagggtcaat    37020
ggattgctca taagcaacca cattaccatt ggcatcatat acaggcagca gtggttcatt    37080
accacgttca ccacgagcca gtgctttagt gatacggtct acggaaggct tgtcagtgat    37140
acgaccagct accatggttc ccatagtaaa gcccgtaccg agatctacac caccagcagt    37200
attacgaacg ttctgtaaga taccttgcga gaaaggagcc tgtgcctgta ctggtgcaaa    37260
gtagtagcta cgtgctggtc cacgattagc agagctaccc tgataagtac caagacgtac    37320
ataggatttc tcaatcaaat cagcaaactg actatcttca gcaacaatca ggttaacacc    37380
ctgcttgttc tcgctaggga tatatccttt gtactggttc aaggttgcac gactatcaga    37440
cttagcttta gccatttcat ctttacgctg accaaccaga taagaagtag caaagtccat    37500
gccttcaatt tctgtctgag ccagtgaaga taacatctca cggtcagtct tattcattgc    37560
ttccagtgca tacaaagtaa tcagtttatc caactgagct acatctacaa cagaacgtgt    37620
agtcttacgt tcacccagta aacgagaaat tgcagtagca ttacgtagca ggttgttacc    37680
aaccgtacct ttaatcatgt actgagccag ttgcttagat ttacgattaa tcagaggcca    37740
gtttcgtcca gcttgtttct gcaaatctgc ttccagttta ttaacctcac ggtcaacaat    37800
cttctggtca gtcagcaagt cacggatttc atccagagac atagtgtcac gcagaacagc    37860
taagtcagtt ttacccatac cagtatgcat tgctttccac tcttcattag tcagcttacg    37920
gctgaactta gatgcgatag tggtaggcaa gtgttcacgg aactgttgac ggtcagcctg    37980
tacctgtgca cgtactgcct taatcaaatc atatacagaa gcattgccct tagtacgtcc    38040
gattatgtca ttaaccaggt catggaaagg ttgccatact ttaccctggt tcattgcagc    38100
cataacacct tcagccacga ttgcaccatt cttctctgta gcaatagcag ctatcagttg    38160
tgcagcatga gcagcacctt taaccaatgg gttcttagta ttagctgcaa catcacgagc    38220
accttccaga gcacgggtag acagtacatc aatagagtcc accagatact ggttagcacg    38280
gtcaatagca ttaccactag gagtagcaac ggaatcatag aaggactgtg cattgagact    38340
tgtctgcatg attgtctgag ccagtgcatc cataccttcc tgtacgttgg tagctttagt    38400
atcaccagct acacgagcat tcagactagc cattgcagca gtaccaatgt tagtcagcat    38460
tgcatcaaca gtattgcctg atttcttatc tgctttcatg acaggaatgt cagccagtac    38520
tttacgtact tcttcactta ccattgccag accaacaaag gtaggcagta aagaagaacg    38580
accctgtgca tcaaactcaa tgttgttagc acccataatg gtatcgaact tctgctgtgc    38640
atagtaacgg tcagcagggt tagtactatc cgggtcagtc atgaacgctt caacggtcag    38700
gttcttagta acatgtgtgt agtattcctg tgcacgagcc atagcagcag ggttaacagc    38760
agcctcagta gccagtgcag caacaatgtt agtaaagagg cgttgttcct gcatattcat    38820
ggtgaagcca tgagcctgaa catcacgagt tactttagtt gcattcacta ctgcatcaga    38880
aaacttacct tttcgaatta cttgctgtac tggttctgaa ccgatgtagt cagtaatcag    38940
cttatcaaaa gtcttaccta actcttccag acgagtattg tcaccatatg ctttgttatg    39000
```

```
gaacagggta gtgtctttgg ccacagcagc agtaggagct tgtccacgca ttactacagc   39060
agagttaaac agtaggccag agaacatatc atctgcatta gccggagctt tcttacgtcc   39120
aaataccaga cgcttgattg cttcatatac agcctgaacc atagctttaa gtgcagtggt   39180
tttcttctgc ttaccaatca attcacggtt ggttaagccc catgccatgt actcattcaa   39240
tgcagcagct ttagccattg ctggttcaat gaagccatta gacaaatgac cattaatggt   39300
attgagagca tcagcatatg cttcacgtac tgccggqggt tcattcttaa catccagagt   39360
acggaactgg ttcatcaggt cttcaatgtt ctggactgct tcattaggag tgccttcata   39420
gtgagccagt acagattcaa aagtagaagc atgaaccaat tcatgaacca gagtctctaa   39480
agaaggagta actaaataga tggtcttatc atcaaagtta gtccagccgt atgcattacc   39540
tgcttcagca gcttcaatat cttccggtgc tgggcgagta atattcttct caatagcgta   39600
ggcatccagt tgagaaggcg taccataaac aaccttgtag tctttagcag caagggattt   39660
ctgtacttct ttcaatactg cttgctgttc tggagacatc tctttagcca gcttagtgat   39720
agcagtattg gacaacagac gtacaccaga cttcagtaca cgaccaacct gttccattgc   39780
cggtacttct ttagctggtt ctgctttagc agcacgtact gcatcacgac gcttatttaa   39840
ttcagcatca aacagttcgt tcagcttttgc tacttgctgg tctacagtca gaccttcaag   39900 agaaattta ccgtcgttca catatggagc accaacagca gccatctggt caacagtgac   39960
ttgtacctgg ttcattacct tgtggcgaat atctacaccc agagcaatgt tacgcaggtt   40020
acgttcaatc tgttcagcac caacacgtaa caggtcatca gtagcacctt cacgctggtc   40080
atattccaga gcagacttag cgatagcctg tttggtttta tcagacagtt tgctgaagtc   40140
tacattcttc atgaacttag cgtaggagtc ataaacattc ttgatagggt taccctgcca   40200
ggaagtatat acagcctcat tagctttacg acttgcatca gtaatgtcat tgataccaat   40260
gttcatacca tcaaagattt tcagggtatt cttcggagca cctttcatag tagaaagggt   40320
ctgcatcatc atgccatcac cagtaccgat ggtcataaat ggaatacctg ctacacctgc   40380
ctgtgaagga gcatagatgc tcattggcac acgcatacgg tcatctaagt tggtagccaa   40440
tacttggtta gcaacatcag tattctcact accagcaatg tagaaagtct gtgaaccagt   40500
ctcaatcatt ggagccagtg gagataatga agcctggatt tcattcagtt ctttctgtgt   40560
taagaaatca cccttcttcc atgttgggtc ttttcttt tctgccagtt tctcctgaac   40620
acgttgctgg aacatgtctt gcagaaccag agattgaatc tgggtagctt tctgcaaatt   40680
ctcagtagag tacatcagac cttcacccac ggtatttcgg ataccagtac gcattggttc   40740
aacgaacaga tggagcatat tctcctgcaa gttcttcaga gcattacctg atacagtaaa   40800
cttctgaggg tctaacttac cagtcagagc accatctacc tgctgaatag acaactcacc   40860
tttacgcata accggaacat taccagttag tgcttccata gaagtaagga aagtatccag   40920
catagcctga gcatcagcct cagacgcagc ctccttacca aacatagcca tagctgggga   40980
aatgctaggg tcagcagcac gggcttgtag aacgtcactg aatcgttcat agatgacatc   41040
agtaattgca ctaaccattt tgcctgcaat accacgagca ccagaaccat agatggtaat   41100
agtcagtggg ttttagcga taccacgttt caggtccaga gtaccatctt cattcaaatt   41160
aaagtcttta atgaacaggt ccattaactt ctggagatgg ttcatctggt tcataacagg   41220
aacgttgtta cggtaagtac tacgtaaatc attcagtgct tgttgcagac cattagtgga   41280
tgcttcatac aggtcaacgc tgtcctcatg cgaatgatgc tcgttcatgg tcttaccagc   41340
tttaccgaag aacaaaccac ctttggcagt attcttaatc cagtctgggg tgaacttacc   41400
```

```
accagtcatt aataccattg cgttgattgg tccgttggtt acaccatcag cttcaacgta   41460
cagtggggta ttaaagttgg tacggtcatc actgttaagg taacgggcat attccatcag   41520
agccataaga gctacgaatg atttatcact acccaaagaa gtcttcagaa tatccactgc   41580
atcggcaggt aagtgtccag acttatcaaa ttcaaccatc atatcaacgg caggtttaag   41640
tttgccttcc agagctttag tcagctcatc tgacataact tcacgggaca ttttatgaac   41700
tttgataccc aatgcctgag ccagtccaag ctggaagtca gagaacgttt gactgttttc   41760
attacttaag tcgatggtag agaaggttgg aaggattgct tcacgaacca gcttactgga   41820
ttgtgggttg ttcttaccaa gcatctgcat acgacctaca cgggtcatgt tgtagccgta   41880
gtgaataggt gtatccagtc cattctcctg ttccttaatt tgattgatta caccaaacaa   41940
ggaatcatac gccatggaca cggacaggtt tttaccttcc agagacttag cagtattcac   42000
attcagcaat tctggattaa gagcaccagc acccattaac tccagaatgt tgtcacaacc   42060
caatgcttca tagaaattaa ccatcggcat atgtacacga aactcagtag cttgttctgc   42120
tttgagagca gctttctgtt ccggggtatt cttaacagcc gggttacgta actgagtttg   42180
agccacggaa ggaatgtcat cacccagata caatttctct actggttcta aaaggacagt   42240
ttcctcaata gcagtaggga atttattaat ggcatcgtta tcatccagct tctcaatggt   42300
atacagacca acagtcttat tagattctgg gtcaatctca gacacatcta acatggactc   42360
tttaacttca cccatctcaa taagggaaga cagaatctct gtagccattg ccattgggat   42420
acccttggta tacccagag gtgcattagg attacgattc aaaccccaat aggattcaat   42480
cttttgagcc agtgagttag tagcttcaac cagggtctga gcattctcga agtcagccag   42540
aataccttct ggtagcagag atgcttccac accagtaata gcagctacgt ctttcatgtc   42600
tttaacagca gcattctgtg tagcagtcaa tcgccattgc agaccagcaa gtacagcagt   42660
ttctaatagc tggtcattga acttaaaggt gtcaccatct ttctctacga tgttaagtaa   42720
cttaccacct acccaacggt tagcctcagt accttccgca aaacgtttac caacgttctt   42780
gttagcaagg aacttagcca gacggtcaga cagagtagtc ttcagagttt caccaaactc   42840
aaataagtcc tgataacgct taatcacatc acttgtgaga gcgttatttt cttttttgagt   42900 gaatgcttca aagcgagcag cagaagacag tgctttctta acatcagtca aaggagattc   42960
agaaccaatg gtacgagact taggctcttc tggtagggaa aatgctttaa ggaactggtt   43020
tggtgtctta tcattattat agacagggaa cactgtttcc atttccgata aaggtttacc   43080
accaacggta tagtctgctt tcagttgagc cagtgatact tcttccttct caacgttatt   43140
ggtattacgt tcagacgtat ctacaccaat ctgaataagt gcattgtttg cttcaacgaa   43200
agattgaaca gtattgaatt gttcagcagt cagtttctga ttatcaaaca gttgcagaga   43260
tacaaatggt tgctcactac ctttatagaa ggtagagcga atagcaccag tatccagaga   43320
catatcacga taaccatcat gcccaaatac gtcggacaag ctgatatggt cgccattaga   43380
accaaccaca gtaccatcag caaacaacca agggctttct ctacggtcac cattcttatt   43440
aagagtttcc tgtgaaatag tatttttcttt cacataagca tctctttcag attcagtagt   43500
agagacttct tctgcttttg gactagtctc tttagtagga gcagtcttat tttctaccac   43560
tggtttatct ttaggctgta cagtagtggt gtcctcttgc actagtgcag gagtttcatc   43620
aacctgattc actggttcat tagtctgttg agactgagtg gcatcaagac cacccttgacg   43680 gaactcttta actacctggg cagctggctt gttcagacgt gaatccaacg aggtaacttt   43740
```

```
cacatgagaa acattaagct ccgggtaagc cgtagcaagt gcgttagcaa tgtcagctac   43800
ggtcttagct tccagtgcta cttgctgggc aaacttaaca gacttgatat cgtaaggatt   43860
gacaccgagg ccagtacgac tacgtaccca ttcacgggaa ggcgagagag cctgataatg   43920
aacagactta ttcttatccg cattccccga aatcagatgc tcattcaacg ctccgacctt   43980
attctgcatg tgctgggcga acttcataaa atcgctcaga taagcggagg ccaaatcgaa   44040
gttaccagag ttatacgcag aacgaatgcg tttcgcatgt tgcaacgcag agtactgtcc   44100
ttcattagaa cgagactcat cggttttaat ctgtttacta acaatatctt gaggacgtaa   44160
gcctagttct tctgctttag cgtcgaactc tcgtgcaccc tgtaataagg cagcagcaga   44220
ttgcagggca gcacgttgac gattccccag tgtaatctta ccttcacttg catgtttcag   44280
aaccatgttc actgaatctg catccagcac ttctggagat acatcagcag ccatagcaat   44340
gttgtttgct tgggcttgat tagcttcttc agtagctttc agcttacccg cttcagcctg   44400
ttcctgaatc atggaatgga tggcacgaaa tgcacggagt actttagggg tattctgtac   44460
gttagccatc aggccggaga attggtctac gattgcagca gcaggggaat cttgttccag   44520
attagccaaa gcacccgggt cacggttaat gaagctatcc atagacatga tattgtcata   44580
catctggatt gcagcttcca tttgaacgtt agggtcttcg gcagtattaa ccaagtcagc   44640
catcttctga atagcttcta cacggttagt ggaaccagaa acagcttcac ggattgctgg   44700
gttagtttgt tccaattcta ccgggtcaaa cttcattgcc tgagttaagt cagcagcata   44760
ctgggtagca gcagcttct cttctggaga aatatccatt gcatccactg cttcctgaac   44820
agttgcttga gcttgttctg cctgagcagt agcttcttgt gcagcagcgt taccgtagc   44880 atcagatacg ggggatgctt gttcattacg cttagcaact tcttccccac gttgaaccag   44940
gatgttagta ataggagaag ctactttgc tagtgcctta ccagccaaag aagcaccagc   45000
cagggtagta cgtacagcag gaccaacggc agcaccagca gccttaacag ttgcaccagg   45060
agcttgagca actccagcag aaccgaagcc atacaatgaa ccaagaccgg tttgttcacc   45120
cacaccttta agcaaatcac gcttagcatc tacattacct tgaattgcct tgttctgtgc   45180
aaactgactt gtaccagact ggataccttc ttctacagtc tcacgcagca tgttagaacc   45240
agcaccagcc agtgaaccta ccttaagtgg attaagttca aacttggata ccagtggacc   45300
agtaagagca gcaaccggag cagttaagcc agcagcagta atacccgttt cagatgcagt   45360
ctggcgacgt gcttcttcag gagataaacc gtctttaata tgctgttggt atacaggaga   45420
tttagcagcc aattcactga atggcatttc cataatttca ttagcagtct gttggtatgc   45480
accaccagct tccataccac caattgctat agcaggtgca gcaacacgac cagtagctaa   45540
tgcagtacgt gcaggacgtg aacctaactc agcagctaag gtaatgcctt taacagcttt   45600
atcaccacct accattactt taccgagtgc agatacacca cgaatcaatg gaccgccggt   45660
aaagagagaa ccaacaccct cagccagacc atcagtagca gccatgccat tggacaaggt   45720
gttagcaaca gaatcgtaag catctcgacc aatgcgagac agggaagcaa cgagatcact   45780
ttctccttta gcaatatcct gcttatagag tttctcgttt tcctgtgcag atattacgtt   45840
ctggttctgt actacattac gacgagcatt taatgcatca gactgtaggt tgtgtacacc   45900
tttattcaac cagtcaagac cggaagcaat ggttgccccg gcattatcat tgaccaagcc   45960
tgtaccaaga gcagcaatgc ccccaagagt attagcaaca ccaagaccaa caccagaaag   46020
ggtatcacca agtgcttcac catatgtacg actcttagtt aaatcacgac gaacagcatt   46080
agctgcattg acacgagcat tgagaatgtc cattccttgc tcattgccat acttgtttat   46140
```

```
gatttcaaga ggagaggcat tagtaaaatc tgcctgaaaa gaacctgggt caaatgcacc    46200
agcacctaag ttaccagcac ggcctgcctg taattggtaa gcgttctgtg gggttagttg    46260
gaagggcttt tgcccttgtt cagcttgttt ccgagaggtt gcagtagaga catcgacttg    46320
cttagcagta gtgatgctgt ctgcgaaacc tgccagacgg tcaaatgttg acatagcatg    46380
attcctgttc aaacttatat cgtataagaa gattcactgt acagtaagtg aatgtaagag    46440
aaaagccccg gatggggctt tattagtatg taagattttta tcgaggttgc atataggggag   46500 gtaaaccctc tgctaatttt cgataacgtt tagctcgttc ttcatcttca cgactacgtt    46560
cacgttctac tgaagcatta gaacggaagt tctgtggaac cagatttccc tggtcagcta    46620
ccacagtatt aacagcagca tctaatgcag ctcgtgccct tgctaactca gcctcacgag    46680
cagggatagt agcagcaagc ccgctttgcc cagcagctac acgacgacga gtatcagcaa    46740
gtaaggcttc tgcttgtgtt acctggttct gagcattagc aatattaccc tgtacctggg    46800
taagaacatt atcacgagca gtagcttcaa tgccttcccc acgacgtact gaacgtgcta    46860
gttctctggc aacggtatca tcaatacgaa tacctccacc accttcattg gagatgaacg    46920
gattaagtgc atcaagtgct cgactaatca taccttccgg tacgttggta gtagactgct    46980
taagaatctc agcagctaca gcaggagact gcccggattc ttgcataaca tcattgagtc    47040
gagcaatcat ccatccttttt tcagaacctt taaaagcatc cttaagaaga cggtctgcta    47100
cttcaccaat agtagagttg tcacgtaatg cacgagcata attagcagta atggttccag    47160
tgttatcttc agactgacgt gcagcaactg tattgcctgc catgtttgag actacttgct    47220
gagtctgtaa ctgatcaagg ggtgctccta cttctgcctg tgcaattaac tggcgtgctt    47280
cactccacgg catatcctta taaccaccta cacctaagtc aggcaatgca gcccaggtct    47340
tagaaaggtt accattctta cggtcattga agattgcttc agctatttttg tcctgtactt    47400 caggagtcat ttgctgatta cgccaatctg aaccaagcac tttaggggca tagtcttcca    47460
gagtagcttt attaatctga aatgcaccta caggagaatg accttgtgac gggttattaa    47520
tcatactctg ttgatgatta gtaacctcac ctagtgtcat ctcagtaata ggcttatcag    47580
tagcagcaaa ggtataggtt gcatcataag gagaaccaga acgagtacca gcagttcccg    47640
gagcagagcc agaaggagac gtagcgtaag tacctgggaa tctctggttt acacctcgca    47700
tgattgcagc acgtacacct ggagaagcat tctgcatagc agactctgcc aatgtaagag    47760
catccatagg agtggaagca ctacggaaaa tatccgtcag tataccggat gcagcttgtg    47820
aatcagcatc attacgttga gccacaccca aatcaaagcg gttctgtgct tggttaatag    47880
cctgaccacc ttgcccttga agacggctca gcatatccag ttgttggtcg gcagggagtg    47940
cagataatgc atcacgggtt tggtccaatg cagtattaat acggttctgg tcaccagact    48000
gataagcctc agacaataaa cgaatagctg gagaagcatt atctaatgca gagtcagtat    48060
tctgtaaacg accaaaacga taagcattgt agtcattaat tccctgctga ccttgttgag    48120
tcagaagagt acttgctcgc tcatccagat tctgcagggt atgttggttt acgagtgaag    48180
ggtcaacccc ctggaacaat gcaccggatg ccagagcatt acgatactca gtagggtctt    48240
gatactgcat agcattcatc atgacggcat tgccagcctc ctgcttggca gcgttctgga    48300
agttacccag tgcatcactt aagccggagg tggcgttacc aatcatgttg ccaaatgtgc    48360
gaatgctgtc accaactcca gagaagttag gtgcatcaac attacgccat gtaatttgag    48420
ccatgatggt ttcctattaa cgagttagct tattagctgc aatgtaagca tcagctgaag    48480
```

```
actggtcacg gttctctgca acagcacgac tacgagcacg gtcttccagt gcagtgttat    48540
aagacttaat ctggttgttc aggttagtgt tagtaacact cttagcaaag ttcaactggt    48600
ctttggctaa cttattggcc tggaaaccac catagatatt agctaatgaa ccaatagcac    48660
ctagtcctaa ctggaaggtt ggtacgttca gacccaactg attagctgaa ccagacagga    48720
aagaagtagg ggtagatgca cccaaattag tacccatacc aatagctgca cctgggttat    48780
agttcatagc tggggtatta aagttcggat tgttattaga catccaagac atagcagctg    48840
gctgtggggt ttgattgcct gttaagaatg acaaatccat ggggattctc ctgttaaaca    48900
aggtcagtat taagggtcat gtcagagaag ctgccaacca tgtttaaaga catgtcagct    48960
atatctgaac cagtcataag agtacgagat aagaaagaat ccatcgactc cattgacacg    49020
aattgcattg ggtcaattac accctgccca gcagtaccaa acatttcttc atactgctta    49080
ttgattgcca tcatatcagt attgtactgc tgcattacac tctctgcttt ctgaatagta    49140
gcagccgtag atgcattaat atactggcta ataccattac ctactgaact ggtaagctgc    49200
atgatgttct gagcattcat catttcactg gctaaggtag ataaggatga accagtagat    49260
agagcagtac caacattcat agctaccatt gaagcaacag cagcaatgat aaaacctagc    49320
ttatcaccaa agagtgaagt ggatacttta gtgataatag ataccagaat cattgcagca    49380
atggcgtttg ctacagcacc tactattaca gcagctaatc caacaaaacc gagtgacgcc    49440
ccaactgctc catatgcccc aagtatacct gcaccaccag tacccatagt gaatacggat    49500
acaacgacag caaccacaac aaccacaatc ttaaaggcag atgtttgata ccacttctgc    49560
ttaaccttct tatatgagtt catcactaag taggagcagg cagtggatag ctgagtactt    49620
cgaatcagtg acattgaacg atagatgtta gtatgtagtg gaataatgaa cccactctcc    49680
tctgcatcac ccattgcttc ggcaacatca atatgcactg acttattctt atatccctg     49740 ttattgtgat ttagacccag tactctaagt ttacggtaag tgttattacc atcctgccaa    49800
agcagttcat actcctgcat agaatagaat gtagtggtaa cctctaactt cttagctgaa    49860
ccggagttac tagcagttcg tatgttcttg cgagtaagag ttatatcccc tgcatacctg    49920
gctcgaagtt gtccttgctt agcaccagac catgcttgcc ctgagtgggt agtttcagat    49980
acgtaattcc aaccaatggt catgtcatac ttgtaatgct tattactatg taccctaaat    50040
tctctcttag gtatgactgg gtattctggc agtggtggag gagttccaat agtgtgccct    50100
tcagtcctat tccaccattc tacatatgca tcaactgcat cattagctgc ctgataacct    50160
gcaatcactg cctccaaggt tggataggtt gggtcaggtg ggaatgcttc agtagccatc    50220
tgaaagaaac ggtagatgta ttccttagca gtatcttcag gagtattaag agatacgcca    50280
aatgtgccat aaatgtactg aatatcacct atatcatcat tcttcttaag ctctgttact    50340
accttatcaa ttttttccacc ggtagcttta taaagagctt tcttacagta tggatagatt    50400
gggtcattct ctaccccattg tttatcgttc ctgattggaa taaatggata gaatcgatta   50460
tcggtagcct cagtatcgaa cagtgagtct agtgcaacgt taccagagtt ctgcttatag    50520
ataagcatct taggtgtacc aacagcagtc atctctgtat ctgtacgagt agtctgggag    50580
gaatacttac gaaccagtgt ctctgtggtt gtagtaattg tatcagtacg agtaaccacca   50640 ccacctatat caactacgtt ggtagttaca gtagtgctgg attgaatctc accaaactttt   50700 ttatgagtca ttccctgtc agatacaact acagttacat catcgggttt ctcagtgaat    50760
cctttacgat aaaccttaac gtaagagttc cagttatcca cacttggttc agtgacagta    50820
ttgtcttcat ctggtctacc atcagagtaa acagagtgag tatgtatggt cttagtaagg    50880
```

```
ttagttgtat tagctgttgt atcacttgat atggtagtcc atagcaaagt ggaaggtaag    50940
tcaccctcac tatcatagac agtagtcggt cctactaccg gtggattggt agagggagat    51000
ttatagaaag agtaatcagc atagagatac aaagcacctg gttcaaagtt agtaggtgtg    51060
aatttaatag tagaaccacc atccagggag gtcatagtaa tttcattagt atcttcattg    51120
atgtctatgt cgaatcgttc catgattcga ctaggagcat tttcataaag atattggtca    51180
caccattgct caaagtcagc aaagccaatt tctgctgcct gaacatagac agactctcca    51240
gcaggtggtg taatttgacc ctctataaca gtagggtcaa tcttagccaa tacacccaac    51300
gaagaaccag ccataccaac ttctgaatca tagtggttct tactccagct ggagaacaat    51360
cgcatacgaa taccaggtcc attcagataa ctatcagaga tagtgtctgc catagtgaat    51420
cctgtattgg aaacaatgtt accgatgact acagtcttca tatagttagg acgtttgtgt    51480
atatcccctg ccatgttata gacagaggat gctacgtata ctttagtctt cccactgaat    51540
aagcccatat tagttcagcc cgttgttagt cttcagcttg gtcaaaatgg tatcaatact    51600
tgcgttagtg aaaccattag gaggattcaa gccttcatca atagtcttct gtgtaatcca    51660
tgcatcagta aacaacttag atgctttgac ttctgcatca cgttggtaag aagtaatctg    51720
ttgagagtac aactctttct gtttacctac agaaccagta acagtagcac catcactacg    51780
agtatccagt gtctgtgcac gttgtgcttc tgtctgctca gtaagcaatt taagctgttg    51840
aggtaacatc tgattagcat taaacaatgc agcacaatac gtctcagact cagtagcaat    51900
cttcatctta gtaagagcgt attcactctt agcagacaat gcctgaatct tagccagtac    51960
aaactgagcc ttagaagtag ccagttgaac acgagcagta actgcctgaa tctgtgccat    52020
agcagcagcc cagtatgcct ggtcacgtcc aagtaagaac tgaacagcat tactcatgca    52080
tgattccatc atagcaatgt atgctttggt atattcacca ccagtaatac ggttagcttt    52140
aaactcagct ttaaggtgat tgtgagcaga ttccattaat gcatcaaacg taccactgcc    52200
tcctacttca cgggtagtaa gagattcatt ggttatttta gtaatagccc caaagattgg    52260
agaatcatct ccaccaggga tatcccattc aggaccagac atatcaatat caggaagggt    52320
aaagtcatca cccttagtta actcttctag gagtcggtta gcttctacct cagcagaaca    52380
agacataatc attcctcttg gttcaaaaag aaacggccca cggagttacc ccagtgagcc    52440
gtgttgaact gtagcttata cgttaatcgt taaggctacc agcagcaatc tgtgcttgag    52500
ccagctgagc caattcagct tcagtcaacg gaggcagtac ttcaatggag aactcacgtg    52560
cttctgttgc acgaatgtct ggtaagccat tcttaccttt acgagtagta atgttaatga    52620
acttacgttc tttaaggaac tcgtagatac agtacggaat atgataacca ttgtcggtta    52680
cttcaccgaa cggaacaaac ttacgtacag tacccatata ttcgttagct acggtgataa    52740
tttcacccgg caggtctttc ttcttagggt caaggttctg gatacgtaca cgaatcagtc    52800
gagtctgttc tgcacgaatc ttctgaccca gggtcatctt cttaacacca gcttcctgct    52860
tagcacccaa tgggttaaca gcagcttctt ctactactgg ttcatctttt acttgtgcag    52920
cttcaatctt ctcacgaagc ttttcaacgg aaatgttgtt agagaactta atattcatca    52980
acgttgcacg ttgcttaaga acttcaagtt cgctaggcat tgcaatatcg ttaacggtat    53040
cttcgttgcc ctgtacgttc acttctacgt cagtggtcgg tttatcgtta atgctcatgt    53100
tcatatttcc tgtggttcat ttagttttat taagagggg acttatgtcc cccttgtttt    53160
atttcggact attacagagg agcaacagtc ttaatcagag ccagacgttc tggacgttta    53220
```

```
accaggatac catagtacca cttgatagaa ctgaagccag tttcgccata cgggtcatta    53280
cggtcagcag tttctttacc cggcatctta gtcatgatgg tgaacttaac agacttacca    53340
tcagtctgga agccaatggt agagaaggag tcatcaccaa ctaccagcat cgggaatacg    53400
tcgtagtgtt cctgaccaga taccatagag gtacggtaac ccgggttagt agtaacctga    53460
gcaccagcac ctgcccaatg cagcatctct ggaacctgga tgatacggaa cttatcaata    53520
caaccaattt caccattcat cagagtacca gcatcagcat agtgctgaac ttcgatgaat    53580
gctttattac caaacaggtc tttcatcgct ttcagttctg gaaccagttc agaaccaacg    53640
tacattacac gagtaccacc gagtactttg gtatctgtca gtttagaacc agtgatgata    53700
gtagtctggg tcggggtacg gttctcagta agaatctggt caagacgcat caggttctta    53760
taagaaacta cagacggggt agaaccttca ccagtaatgg tagcatcaga gacggcagca    53820
cctgcataca gtacagtacc agcagcagcc agcaggtctt tctggagaac agcttcagtc    53880
aactgtacag caccgttcat cagttcacga gacaggtgtt ctttcagttg gtcatcagaa    53940
tcaaagtcca aggactcttg agtaaattcg tagaagaagc cgaatttatg aatagagcct    54000
tcacgagcca gacgagtaaa gcctacacgg ttaacgacac caccattctc tgacagcaga    54060
ggcagtttag aagtgatgtt accaacgtct ttggaagagc cataaaggtt accgttaacg    54120
atggtagcac cattagcatc aatacctgg tcgttaatgt tcttatcgtc gagcaaagga    54180
acatactcgt acaccttaac agtcttaccg tagttcttcg gcatgttaac ggtgttagcc    54240
agaggcataa aatactggtc tttacgagac tgaataatag ctttcttcag ccagtaatag    54300
gtattcatct ggtcggaacc agcaccatca atgctagatt tctgaccgtc aattggagcg    54360
ttatagttta acatatcatc tcattcctgt ttaaagacta cccggtactg ggagtttagc    54420
gaaatcttca tcactcatag cgagtgggtt tacaataggt gttgctttac gtgtagcagc    54480
ccgattaagg gaagctgctt tagcttgctc actgttagcc agagtctgct taggttgtgc    54540
cacacgcact accggctgaa ctgctggttt aactgcttgt actggttcag cttagctac    54600 ttggttaaat gctccttgtt gtgcaagaag gttaccaacg tagttataag cctgaataaa    54660
cggagtacct accggaatct gacctaacac ctgaagacga ttcacttcat tagcaatggt    54720
gtcataaata ccattctcac gctgttcgtg aatggtgtgg agtaagccac gattctgata    54780
aagagcatct ttactggcag catcccatgt cgagctaata acacctaatg tagcttgtcc    54840
ttcttgagta gactttaagt cgtcaatttc ggttgcaaaa tctgcttcgg tgtctgtaac    54900
acggtgtttg ccaccctggt agttaatttc ctcttctgga ttaaagtcca gaggatctgt    54960
accagagtct ttcaacaact ttttaatggc ttcaggattc ttcttatcca ggtcaatcag    55020
gaaagaaagt ttttcctcat ccattaaacc gttgttctgt agcatcagca ttaccttacg    55080
gtacggctga agttcttgca tcttacgagt atagttagca cccatctgca tcaggctaat    55140
ggcctcctcc ggtgaacggg gagtaatcat tttgccgtta gctttaaaag gagccatcaa    55200
cttctcgtaa ccttccttat agttgaagtc agcaggcaga ccttcagact gtttgccttc    55260
ttctttctgt tcctggcctg gttcagcagt agaaggttca gcttcagtaa tcggcttacc    55320
gttactatca acttctgtgt caacaacttt atcatcaact ttatcagaag ttaaagaatt    55380
tgctgaatca acttcatctg gttcagtttc aggggaggtt tcttctgttg gtaggtcttc    55440
aacagcaggg gtgtcaactt cttcatcagg agtctgtacg ccgttggttt ctgggttgtt    55500
ctgagtggaa gtatcttcct cagcaataat agctggggct tccatattca gaatctcatc    55560
atccgacatt gcgagaatgt cggaagctgt ggttgcagct tccgtagtca taggaaatat    55620
```

```
ctccggttaa ttattcgtct tcgggttcag cacgaactgc atcgagttct tcttctacct    55680
gaagaataac gtcagcttca ttttcaccca tacgaatggg gaggtcgagc caacgacgta    55740
agtgaccagc agcttgagcc atgttaagtg catctgcacg gttattcggt tcaagcagtg    55800
ggtcaccaga ctcctgcacg taacgtgcac aatcttctac acagaactgt cgaaggatta    55860
ctttacggaa cagtggattc tccagaagtt tacgtacatc ctctgcgtgt gcaactgcac    55920
ctttagcagc ttccagtcga tgttccagtc ctgcgattgt tgattcttta ctcatgtgaa    55980
ggtctgcctt ataagttcat accaagagcc gatgctgggt cttggctagg gtcataaaat    56040
tgggaactaa gagaataagt cgggtcttgc tgtgcagcta agtcacgttc ctgtaaagag    56100
ttcccgttag tcaaagcgtt atatccgaca gcagcagata tgttgggggt agtttcacct    56160
tctttagtag gtgttgtcaa cgccttagtt atttgaaggt tctggtttcc ttgagattgt    56220 gcttttgtt tttccatatc acgagcatgt ttagtaccag attcctgttc cagataatcc    56280
aggtctttaa ggtcaccact agaaatagct tctttagcct tagcattatt gagtgcaatc    56340
ttacttttca actcttcatt ctcaagctgt gctttctgaa ttgctaattg cttaagctgt    56400
tcttccatag ggtctggttg tggtcgccag gtacgtaatt catgagcaag gtctggcata    56460
cgtttaagtt ctgcaatctt agctacaaga gataatgtaa tagtctggtc aactgtatta    56520
cctaacgttt gaaccatgaa gctcaagtcc tgagatttct ggttatcaat ttcagcagta    56580
ttaatatcaa cctcaatatc gaaattacct ttaaggtctt cacggttaat ttctacgtac    56640
tgttcattgg taatacgtac tacttccttc tcagataaga atacggcatt cattgcacaa    56700
atcttagtac caatgtctgc cataccctta gctaatcgac gaaggattgc catctcacgt    56760
ttggatgctg catcgagtgc accacgaata ccagcagcca catctccata agctgccaca    56820
gttacacctc cagagaatgc tttaacacca gttagtgctt ctgcttcctg gttctgcatc    56880
tgagtcataa ctattgccga ctgaggtaac tcagggaact tgtgttccat aatggcctga    56940
ctaggattgc cctgcattgg gttgtattca tagtcttgcc catcatcata tcgacgacgg    57000
tttagagtat ctaacatccc tttaggataa ccacgttgcc cgtttgcact tcgacccaac    57060
aggtcaatca tcccacgcat ggttgcacca agaattgctt ggttatcccc caacagttca    57120
gcatcagctt caccgaagag ttcacgttta cgtggcatat aaggaacaac taccaaaggc    57180
aacttaccat ccgggaatgg gttctttttcc atacgaataa gagtagaacc aatccaggta    57240
gcaacaatag gctccagtga accatcatca ttgatgtcgt agaatcccca gtactcataa    57300
gcaactactt tcttacgtag tgcatcctta aactggaagt caccaggagt tttactttca    57360
tggtctgggt cagtcatagg actggaactt cccagtcaa tcttatccaa attgtgataa    57420
cggtctttgt tcttcatgag gtctgctttg cacgtctcaa acgagataac tgcatacaaa    57480
gccttgtcca aatcaccatt acaactcggg tcaataacta cgttattagg attaagcatt    57540
tcaacagtag gtctgttaac cagtgccttc tctacctcta cctcagtaac tccagtctgg    57600
attgcataag tagcttctcc agtttcattg aagtagttaa cagcttcctt aatatcttcc    57660
ggcattgttt cgtcatactc acggggattt tctgcctgaa gctgtaaagc ctgctgaaga    57720
atatctgctt gttcctggtt ctcaattgga tacaactgga agactggtgt ttctgtttta    57780
atcttaacgg tcttacgttc ccaaccaata cgggcaatac cagtaccatc atctacgaca    57840
ctatgtacgt aatcatccac cagttttact ttattaagct gggtacggaa ttggtagtta    57900
agaactaatt cattctgtcg tgcagctaac tcatcctcaa aagtaacagg ggttacctta    57960
```

```
aagagtttat tagatgagag aaatggttca gataatggtg cataacgcca ctctgcctga   58020
cggcgaacca gtctaggttg gacttgtgag cgtcctttaa cctttggggg tttagccttg   58080
cctttgactt ccatcaagtc attccactca cgaatctgag ccatgattgc atcgtgagca   58140
ggtttagctg attccaaatc acccttcagt aattggatac ttggttcctt cttccagtcc   58200
gttaacttct ctgattgagc cgggtctggt aaaggcttaa aagtgtcttg gtgttccata   58260
gttattcctg ttcaaaaagt ttacggtcag cctgaatctg tttacccaac tcaattagtt   58320
ggctgtcacg gagtctaaca gttgcccgga gttcttcaac caaacgtctg ccttcttcaa   58380
gactgttgtc gagtctggct gcatggcttg caagacttct gcactcaaag gttccggctt   58440
cggcttgacg tttatatacc gatgctcgtc tttcagactg ttgcatccgg ctgtcataat   58500
cactgctaac gcgagcaagc tcgcttgcgt aattactctc agccgtctgc aaccgggaag   58560
tgagtaaccc gacttcgtaa ctatggtttc tttggagagc attgtatttg tcctgtaatt   58620
tttgtagtgc cttctgatct caaccttttt gggcatccca cttcttttga acagtagact   58680
gtccattgga attaccccaa aagtaaatgg tggccccgag gaccaccacc agaagataag   58740
gccaaccttt agagattagc atcttcatta catgcctcca gtggcacatt gcctattcgg   58800
ttagctaccc aaccatacgt aaagtctggc atgtttaatg aggtgtagtg gttaagttgc   58860
ttagcatcaa gtaacttaat cattacctga catgctgcaa cttttgcctcg ttttttctgt   58920 aatgctttat atgcattaac agtacttgta ccgactttac catcaacctg tattttaggg   58980
tagtctttgc catcacggga catttcatta agagattgct gcaaccactt agccggacgg   59040
gttacacccg tattaacacc agcatctacc agcttatgtg ttacagcagg agatatatca   59100
gcgaaggcta cgaagttagg cttaagtacg taatcatcaa tgtatatctc agcagccatc   59160
tctttagata aatccttcat agaaccatcc cagccatact cagtagccag aacttctttg   59220
tgagatttag ctacagcttg ggtaatacca tgattggttt caccacctgg gtcacgagga   59280
ttatttacat atccccttc catataaaac actgcccca ggatagcagc gacaactcct   59340
cccactgcac caccttcgt agcaagtttc tgtttagctt tcatgtgaat cttcctttga   59400
tcggaatcgt attaatctgc ctacaatatt taaggcaaac agcgcgattg caatattgga   59460
accatgggga atatcttcca ggatgtgacg aggtaatcct gtcagcattg gttgaatgat   59520
atctatggta gaaaacataa ttaacccgag cgtactaatc tggatggatg cccacttcca   59580
gcatcttttc cagttaggta ctaactctac ttttcttttt agcctgcgaa ccatgcgaat   59640
atctcccgtc ttgcagcagc caatacacca ataattgcac ctgccccagc ccacacccac   59700
ttaccaaaaa ttccagcacc aacaacttta tgcttaatgg tgatgaactc ttcaatagta   59760
ggttcattct tagctaagct atcctccaca tttttagtc tattgcctat gtcattgatt   59820
gaatcccgta gttctaccag agtttcctcc agcttctcac gatcctgcct gtcccttgtc   59880
tggttctcaa acagagtctt caatcgttcc tccagtctga ctagaagcag ttcacctgat   59940
tcattcataa aattaccgta gtgatgtagt tagattcccc aacagggcca tatcataaga   60000
tgactcttag ataatactta gtatgatggg atacatccag acatagtgtc tggtatcaac   60060
aacgaggtaa ctatgtctat taagatatt ttccaaagtg gtaaggatgt tgtgtgcaaa   60120
atgaa                                                              60125
```

<210> SEQ ID NO 2
<211> LENGTH: 6122
<212> TYPE: DNA
<213> ORGANISM: Artificial Sequence
<220> FEATURE:
<223> OTHER INFORMATION: A part of DNA of novel bacteriophage CJ23
      Contig00002; Synthetic

<400> SEQUENCE: 2

```
taagcattac caagcaatgc atctaccatt gggtcattag aactgttctg acagtaagga      60
ttagaccaat ccttctttgc atcaaagggg ttgtgtgcgt tcatcgccat cctcgttgtt     120
caaatttagt ttcggtaatt gaaatacttc cattagccag atcgtaatca acaacctcac     180
cacagatgct ttcatacgtt tgcagatact ctgctgcctt agcgttagct tccggagtat     240
tcaaaccggt gtggtaacga tacccaccc agttatgaag tgccgtcatt aacgtatctg      300
ctaagtcaac ttcctgttct tcatcacccg taagtactgg gtgcttagct tgataagtta     360
cgttaagtgc ctcaaagtgt cgaggtcgca tacactgaat agtatcaggc cgaggggtga     420
agattgcatg agggtctgaa tcgtcgttca gtctacgtcg attccctgag ttatcaaaca     480
catttaagat tttaataaca tcatcctgga aaggtttcat gaacccatcc atgatatacg     540
ggtattgaat ctcaagagta ggcttagtaa accgggagta agcatatcga gattgaagag     600
ggtagtcagt acgaccttcc ttcatctcca caatgcaact attagttcta agagggaaac     660
gactatgcag tcgtaccagt ccctcattaa tagcagccaa tatctctggc ttactatctg     720
gttcaatatc taatctgtca tcagtgactg caccagtacc cttcaaggta cttaatgcca     780
agccacgata tacttccgat aatttctgca tggttcctca cacaatgtat gaacgtagtg     840
ggttaacact atcttcttct tcgtcatccc acattggatc accctgtta tccaccatag       900 tcatacctgc ttgtggtttc caaggattga gataacccag catggagata gtatcaatac     960
agtcatcctt acctttaatc ccattaatgg tagctagttt aatctggccc atgaacagac    1020
ccataatagt tgaatccctc aactcttccg ggaagtacac cttaccagct ttgaaccaag    1080
gaactaccag gttaaagcgt gacagcttag aggttacagg acgtatgcct ggcttaccac    1140
cctcagagga tgcaaagtta agaagacat tacgattaat catttccttc tgaaggagtg    1200
aaatgaatcc attctgctgt cctgtgattt cgactccaac gttttgtggt tggtattcct    1260
gaaccagacg gaacaggtca tcaaagtttt tatccataag ctgacgatta gccacaccat    1320
caacccagaa ccaatctcca ttagaactat aagcccaaac tgatatgaca ctgtagtcac    1380
tggtctgttt ctccgaagta gcaaagtcgg ttgtaatata atagttgtag caggacttca    1440
tccttaatag ttgctgtctg ctataccatc taatttcact atcctgaacc agtctctcat    1500
cttcagaact aattcgaagc ataagttcct gatagaagcc tgccaactta ccagtcttaa    1560
ctgccatgtc atattgagcc ttgatgtagt cataagagaa acggtcatcc catgcaccct    1620
gaaattcttc tctactgcaa gggaacttct cacacacagg ccatacgttg acatcccatg    1680
caccagactc tactgcttca atgataatat cttctttatt aaagggagta ccattgaaga    1740
ttactttacg acgggtagga tcaagagcat ggttcacacc tttatagacg gtatccttaa    1800
tagcttccat actcgtcttg gagttagcat caccatcact aatcaagtca tccagtacgc    1860
ataatgttgg acgtttacca tatatcttcg taccacgaag acctgtctta gcaccaaaca    1920
gcttaacacc tagacgatgt ccttctacat tacgaaactc taacaggtta tccgtaaagg    1980
tagcttcagg tatccattgc tgaaggaact cactattctt gtaacgaaac tcaatgttct    2040
tacgtgcaga tttagcaccg ttatccattg agtcagatac ataatcatt ccttctactt      2100 tacccaggct tggtaaatgc ccgaacactg ccaggaacaa tgtaaagtat tccatgaata    2160
cagcagtctt acctgcacca cggaagcaca gattaactac atactggttc gggctaatca    2220
```

```
tcttatccaa cattttcagg tgaactggag gtgttttgtt ggattcaccc tctttaccat    2280
taaccaactt aataaagttg gcaaaggtaa gagcaaactg actaggaaca tagttggaag    2340
aattaaggtg ggagtaatcc acctggtcta gccattcatc cagttcctgc ttaattaact    2400
cagacatctg taatgtcctc atctgcacgt actagtttag aaccagcaac ctcttttggta   2460 ggtacaccac tattgattgc attaatttgc tgctcagcta atgcagcaag tgttgccttg    2520
aggtcagtta atccagagtt ctctctcaag tccagattga tattcgttac ctggtctttt    2580
ggtttagcta agtgggtaag gatagagtta gctgcatcac atcttacctt ctcacttgct    2640
gctgtagtca tcagttcaac ctgaacattg attgccttct gataattatc ctggttcaca    2700
atccacactg gaaccaaact ttgttccatg atgaggttaa ctaacttacc cctgtgataa    2760
gcagatacat aagcactaat atctttctcg ctggttcctc gtgcaacaag ttctgcttgt    2820
cggttaggga atgtcttgaa gtaggcttcc ttattggaat aacccatgtg tttataagtc    2880
acatactgaa ctgcattcat gtagtcctgt gtcttaaact taccttcctt cattacacca    2940
gagtaggaga taaagttttc acggaaggac tcagcaacca gttggtcttg ggttatgttg    3000
ttgatcgtgt ctaccaactc ctgggtcaca ctgtttttga agttagcagg taaggcatta    3060
acaatctgct gcttagttag ttcactcata cttatctcgc tacaaagtta tgtctattaa    3120
agaagattct tttcttgggg tgagttaccc cttgaagaaa cgataccata cagttacact    3180
ttagtcatga tatagaaaaa gttcatgata ctaaatagta tgtaatgttc cgatgaccct    3240
attcccaaaa ggagtaacct ttgagaatct atatgaaagc cccagactct agtgacaagt    3300
acttcgaact agaccacact aagattggct tcctttcaga tgatattatc attacacatg    3360
atgaagacac ctaccatgaa ttagctggga tgatgctgtt agagaatcgt ccaggcatta    3420
aagtcttaga accaagagaa acttactctt tagataaaac aatttcatct cttgtgttct    3480
tcacaaaatt acctcatagt gtctccgtca ggcgaagcaa agacagtgtt cggatgacgg    3540
tgacgatgtg attagtcatg ccgcctagta gacagtggcg gtactcgtaa agagttaata    3600
acttctacag tcagggttgc ccggctcctt tcctacctag taggctaacg atacacatgt    3660
atctagggtg atgaactgac ccgtgattga aaacggtaag gggtagagtc gagaggctct    3720
accccatttc tttttctgga ggaatgcaat tatgagcatc tacgcttttg atattgatat    3780
taccggagta cttcataagc aaggacctta tctacttggg gaaccagaaa cagtaagtaa    3840
gttcattgct ccctggcaat ctgtgttctt acctaactgt gaagagtccc atgagattgt    3900
tggctgtctt ttcttatcaa acctacaact caatactgag atacttaccg aaccaaaggt    3960
gtatgacctc actcgttatg acggattcaa tgagttcttc cctggtatac gtttctataa    4020
aatacccggt tgggaattga tagttgacca taacgtcttt aataaaacac tttccattta    4080
cttcagacca ctttcctaaa ggaaggagaa tcaatcatga aattcataat gaccatcccc    4140
agttttgctg aaagggagtc tatgtataca aatgacttct ctttagaaga agtcatgaat    4200
agtagccccc aacatgtaat cctagttcct accttagagg actaccatga agtaaggggc    4260
cagttattct tagcaggtaa tgaccgtaag gttgtatgta ttgtcccacc ttccgtctac    4320
tcctttagtg atgcatatga cgctctacct ttcatgatgg tatccgatga ataccaatgg    4380
gatagtcgcc ataagaatga agaataccat tactactatg taaggaagta agttatgcac    4440
ttcttcggtt taagtagtcg tagtacatgt ccccttaatc tgggagtagg taaatccccc    4500
tggttgggaa taagtaaacc catgaccatg tactatgaac cctgtaaaga agcagatgag    4560
```

-continued

```
ttcataggaa cctgtctaat gttaggtgca cctattacct ttattaagat aaatacttcc    4620
atcgaagttc cagaggatgt cgctgtatac atcttctcct ccagtgaacc tatggtagct    4680
actactctta caggcagact cattaccctc tatccttcct catatttatc tagcgacgga    4740
agctactaat ggttatcagt aaaatttatt cagagctacc tggggatgaa tacacccacc    4800
ataaagaatt aactaacctg gatgctgatg tactcatact ggttccagac gaacagtcct    4860
tgcatgaact acaaggatta ctcttcttat acaataagaa ttcggaagta catctacttg    4920
aaccaggaac accgatgtcc tggcagggta gcttcagtcc ttggcatctc aatacggaca    4980
agtacatact atccttcgag gataacaccc caatctataa ggaaagacaa tgaaactaaa    5040
cacatcaccc tatccggtgc agttagaagt agtactcgac cgggataccT tcattaaaaa    5100
gtacaagaaa cttaaagggt atgagccaga tttggaaggt tgtaaggggt atactacata    5160
ctctgataat aaggttctta tgggcatctt ctcagacccc ttgccaacgc ttatccatga    5220
agtaaaccac ttctgcttat ggtattcga ttatattggt atgcctataa acagtagtaa    5280
tagtgaagcg tactgttact acatggatag cattcttgaa caggtactga agaatgaacg    5340
ttaaactatt aggtatgaaa ggtactgact tactgcacta ttcctctgaa ccagggaaag    5400
caatcattca cattatgtcc tacgaacct caacgctaat aatggagcca ggagagttag    5460
cagactttgc acaggacat aagctaatta ctaacagtaa tgcagagata gttatcctgc    5520
aaaatggtga gtcagtattc ataccatacg gtgattatgt ctatgtattt agcaaagatg    5580
ctaccgtaag aaatagtagt ggtaatccta atcatccgga ctattactct ggtatagcac    5640
gcatcatcac cagaaagccc catcttacag gataacttac acaattaagc tcttaaggat    5700
attaaatgaa acttactaag ataggttatg ctgatggacc tatttccact acccatacaa    5760
ccttacaaga ccttgtacct ggtagactca ctcctattat cctagtacca gatgatcaga    5820
ctctacacga agttaaagga ttagctttac tactaaataa ggtgactatt gtagaagttc    5880
ttgaaccagg aaaaggaatta ccgtggtcct cctacatgta ctcccctgg catgtgaata    5940 cggataagta cactcttacc tttggtatta ccagtgaact gcaaactcct cacttggtat    6000
atgcttcctc ctatttaact gcttataagt aggatagcta tcatattttt gcatatgaaa    6060
agtagcatag ttatgtatgg ctacagtggt gtggctgggg ctacacccctt acactcaacc    6120 at                                                                   6122
```

<210> SEQ ID NO 3
<211> LENGTH: 3789
<212> TYPE: DNA
<213> ORGANISM: Artificial Sequence
<220> FEATURE:
<223> OTHER INFORMATION: A part of DNA of novel bacteriophage CJ23
      Contig00003; Synthetic

<400> SEQUENCE: 3

```
ccatgtggtt cgtactgtct actgtaactt aggtaatctt aaactcctgt atgatttctt      60
aaatcagtac gggatggtta ttggtgtaca gtctgagata gaacttaaat cactccctct     120
gaaaacaaag tatgcacgca tttatggcag gaaccgtagt aataaaagaa ccattaccga     180
ctacttatat gttgatgatg ataaatctgg aatcataccg gatgacccgg cagctacagg     240
ttcctgggta caagtatcca tgacctcaag tggtagtgag tccactaata caaataccta     300
tatagttgtt gggtatacct ctgctggagg ggaaacttct ataccagttg agtttgatac     360
cgttggcata cctttttatta cagtaggggg attcacacag ctcaatggga agggtttcac     420
```

```
atattctact ggtgatactg agattaaatt agctcaggaa ctggaagaag gtgacgaagt    480
tattatgttc cttacaggtg tgcctgcttc cccagatact gttgctattg ataactggaa    540
ggttgttaac tggttataca attttggtaa tgctgtagga ggtgagcagg ttatagatat    600
cccattcgct ttcattgatg tacctgctgt gtataagaat ggggcaagat tgtataaagg    660
tttgcccaat aagtcataca ctgtcgatgc agagaataag agaatcttcc tgacagaacc    720
acttgtaacc gatgataggg taattattac tattgggggc aatcaagaaa taatttatgt    780
ttctgataga acaatccagg aagtagctcg cggattcaac ttacgggatt ctgagataat    840
tttagatacg gatactgtta cctacttgaa tggtaaagtg gttgtgtatg tagcttctca    900
gcagaagtca tacaagctcc ctacactacc aactaatgtc agaattaaat ctgtagtagg    960
ggatttactc acttacgttc cgggtaacat tacagtttcc cttattccaa ttaacattat   1020
ttaagcaaag ggtcactaag tgacctttaa tagaaaaaca aagaggttcg tatgaacgag   1080
atgttcagtc aaggcggtaa aggttccact ggtattctta ccaacaagca agccattgcc   1140
cgtaagtttg gtattaagca gaatgaagtg gtctactttt ctgtaggagt agacttgggt   1200
ggatacaaag tcatttatga caagactact caacgtgctt actcattgcc tgtacttcca   1260
gcaggaacca ttgctgtaag tctcagtgaa catgcagtct ggttcattc agcaggtaca   1320 gttgatttgg gtgaactggc tgctgcacgt agagagtttg tatgcttatc tgattcattt   1380
actacgggct tagtagtaaa tactcgaaat gagcttttga tgcataatgg tattggttat   1440
acctacttag gttctctacc cgtaactatt gttgaaggga ccaaccctgt tggcaacacg   1500
gactggaagt ctcaaacgga tcctaatttg cgtgctcagt ggcatctca ggatggtatg   1560 accttaattg gtagtgtacc tgacgtaact gccctggctt ctgtcggagc aacagtaggg   1620
tctagtgtaa tgctagattc atactcaggc tcttccgttg gtgggggtat tatgattgcg   1680
gttcctaata ctactcctgt agatgaagtt gtaactttca ccggtgcagg tgtggtctgg   1740
aagcgtaagt tctttgaagg tactgctacg gtatatgatg caggttatac tggtacgggg   1800
gatattgccc cattcattaa caaggtaaac tctgccggtt acgattgtct tgtacctaca   1860
tcagggacta tcagtacacc tatcttactg gatgtagcta aggggctttt agtaggagct   1920
aataagtgta cccttacgga actggaaggt gtaacaggag agtattactt aaccataatc   1980
aactctaata cggattacac agctcgtgat gccattaatg ctactgccct attaacaggt   2040
atttcctttg taggtaaagg tactcgaaag atgtgtttgg gtagtagtac tggaggggag   2100
atagcagaat tacgtatatc taactgtggg tttatatcta ccgcaggtat tgagtttaaa   2160
gataatgcat accgtattct atttgataag tgcactattt ctcgcagttt tactaactct   2220
gtaatcttta ttccctggc taatgctggt gaggttataa aattcaacca ctgctggatg   2280
gttgataatg ggggtccatt tacttttgag aatgggcagt tcatctttga ttcatgctca   2340
ttaccagcag gtaaaaaggc aggctacttc gatccagtag tggcattaag tgataatgct   2400
accctagtat ttgctaacgg taatattgag tatcaacctg gcagagcttt gtaggctttt   2460
actgtgagtg gaagctcacg cctcagtatt aaagattcta ctattctgct tccggaaggc   2520
tacagtacag tgcctattgt tagtaatggt gacggggtag ttagtttaaa taactgctca   2580
ttgcccctct acggtaacac aacgattgct actggatttg ccacaagaca gttgataggt   2640
ggctctagca agaaagtaat gtctagaggg tgcttccctc gtgcaggctt tattacaact   2700
aactggaatc taggaagcat tgtaagccct tatattaata gtattagcaa tggctcagga   2760
cagtttgaaa atacatctaa ctggacactc tctcaaactg gaacaggtgc tgtcactgct   2820
```

```
actacagcaa acgatgttcc taacgattta atgtttacaa cttcttttgt tttatctgta    2880
ccatcagcag atgcagcagc taacttcact caaacaatca ttgattgtga accgggtcgt    2940
tattttcagc ttggtttttg ggctaaaaat acaacaacca ccctggcgtc aattagattc    3000
ctggaccagc aaggaaatgc tgttgcggat tccataggat atatcatccc agtggtaaac    3060
acgttcaact tttacgcttt ggtggattgc gttcctccag gagcttacaa agctgaaatt    3120
aattttaatg tttcctctgt tgttgggggc gtcgtaatac acaatgcagt ttacggattg    3180
atttaattaa aactaaggcc caaactgggc cttttcttat atagagttta ctgtttgcat    3240
taccctaacc gatactgctg ttagagtaat tacttgcccg gataagttaa acatacccaa    3300
ctgaatacca tccaccatga atgggtcagt tgaaccaagt gtatatgtag ctaatacgtt    3360
atctctgtta gcaatatccg taccttgtac tttaatacta gcgtctgaac ctactactgt    3420
agttccattg gttcgtcttg tttgcgttct ccattccctt gctgtaccag caccacctgc    3480
aatagttcct gagatacgaa cactaaacat tacctgggta ttcctggttc taacagggaa    3540
cttaagatta ccttcttcaa ttgttaatgc tgctgtaccc ccaggtgatt tagttatcca    3600
tggtaatgaa aagtaattga gccaggactg gtcatttact acctggctcc cggtccatgt    3660
atacaagtcc agaaggaaag tatcttctaa ctctgttggt gggatgggta gtagttcagg    3720
gggaagctct gaaacgttat tagcagaaac tattcgttcc ccatagcttc ccacaaccag    3780
caaacccccc                                                           3789
```